United States Patent
Shelton, IV et al.

(10) Patent No.: US 10,639,018 B2
(45) Date of Patent: May 5, 2020

(54) BATTERY PACK WITH INTEGRATED CIRCUIT PROVIDING SLEEP MODE TO BATTERY PACK AND ASSOCIATED SURGICAL INSTRUMENT

(71) Applicant: ETHICON LLC, Guaynabo, PR (US)

(72) Inventors: Frederick E. Shelton, IV, Hillsboro, OH (US); Michael J. Vendely, Lebanon, OH (US)

(73) Assignee: Ethicon LLC, Guaynabo, PR (US)

( * ) Notice: Subject to any disclaimer, the term of this patent is extended or adjusted under 35 U.S.C. 154(b) by 231 days.

(21) Appl. No.: 15/634,436

(22) Filed: Jun. 27, 2017

(65) Prior Publication Data
US 2018/0368822 A1  Dec. 27, 2018

(51) Int. Cl.
*A61B 17/00* (2006.01)
*A61B 90/70* (2016.01)
(Continued)

(52) U.S. Cl.
CPC ...... *A61B 17/00234* (2013.01); *A61B 17/072* (2013.01); *A61B 17/07207* (2013.01); *A61B 17/1155* (2013.01); *A61B 90/70* (2016.02); *A61B 90/98* (2016.02); *H01M 2/1022* (2013.01); *H01M 10/425* (2013.01); *H02J 7/0063* (2013.01); *A61B 2017/00017* (2013.01);
(Continued)

(58) Field of Classification Search
CPC ... A61B 17/00234; A61B 90/70; A61B 90/98; A61B 17/072; A61B 17/07207; A61B 17/1155; A61B 2090/0803; A61B 2090/0813; A61B 2017/00017; A61B 2017/00084; A61B 2017/00367; A61B 2017/00398; A61B 2017/0046; A61B 2017/00464; A61B 2017/00734; A61B 2017/2927; H01M 2/1022; H01M 10/425; H01M 10/48; H01M 2220/30; H02J 7/0063; H01R 31/00
See application file for complete search history.

(56) References Cited

U.S. PATENT DOCUMENTS 6,783,524 B2   8/2004   Anderson et al.
7,000,818 B2   2/2006   Shelton, IV et al.
(Continued)

FOREIGN PATENT DOCUMENTS

EP   2 923 661 A2   9/2015

OTHER PUBLICATIONS

U.S. Appl. No. 15/634,385, filed Jun. 27, 2017.
(Continued)

*Primary Examiner* — Carlos Amaya
(74) *Attorney, Agent, or Firm* — Frost Brown Todd LLC

(57) ABSTRACT

An apparatus includes a handle assembly and a battery pack. The handle assembly includes a housing and a first control circuit located within the housing. The battery pack assembly includes a power supply and a second control circuit. The power supply is configured to selectively transition from a first state to a second state. The power supply is configured to energize the first control circuit of the handle assembly in the first state. The power supply is configured to not energize the first control circuit of the handle assembly in the second state. The second control circuit is configured to transition the power supply between the first state and the second state.

20 Claims, 11 Drawing Sheets

(51) Int. Cl.

| | | |
|---|---|---|
| *A61B 90/98* | (2016.01) | |
| *H01M 2/10* | (2006.01) | |
| *H01M 10/42* | (2006.01) | |
| *A61B 17/072* | (2006.01) | |
| *A61B 17/115* | (2006.01) | |
| *H02J 7/00* | (2006.01) | |
| *A61B 90/00* | (2016.01) | |
| *A61B 17/29* | (2006.01) | |
| *H01M 10/48* | (2006.01) | |
| *H01R 31/00* | (2006.01) | |

(52) U.S. Cl.
CPC ............ *A61B 2017/0046* (2013.01); *A61B 2017/00084* (2013.01); *A61B 2017/00367* (2013.01); *A61B 2017/00398* (2013.01); *A61B 2017/00464* (2013.01); *A61B 2017/00734* (2013.01); *A61B 2017/2927* (2013.01); *A61B 2090/0803* (2016.02); *A61B 2090/0813* (2016.02); *H01M 10/48* (2013.01); *H01M 2220/30* (2013.01); *H01R 31/00* (2013.01)

(56) References Cited

U.S. PATENT DOCUMENTS

| | | | |
|---|---|---|---|
| 7,380,696 B2 | 6/2008 | Shelton, IV et al. | |
| 7,404,508 B2 | 7/2008 | Smith et al. | |
| 7,434,715 B2 | 10/2008 | Shelton, IV et al. | |
| 7,721,930 B2 | 5/2010 | McKenna et al. | |
| 8,343,644 B2 | 1/2013 | Vaisnys et al. | |
| 8,408,439 B2 | 4/2013 | Huang et al. | |
| 8,453,914 B2 | 6/2013 | Laurent et al. | |
| 9,072,535 B2 | 7/2015 | Shelton, IV et al. | |
| 9,179,912 B2 | 11/2015 | Yates et al. | |
| 9,186,142 B2 | 11/2015 | Fanelli et al. | |
| 9,717,497 B2 | 8/2017 | Zerkle et al. | |
| 9,795,379 B2 | 10/2017 | Leimbach et al. | |
| 9,808,248 B2 | 11/2017 | Hoffman | |
| 2012/0028085 A1 | 2/2012 | Wurth | |
| 2014/0263541 A1 | 9/2014 | Leimbach et al. | |
| 2015/0272575 A1* | 10/2015 | Leimbach | A61B 17/072 227/175.3 |
| 2015/0280384 A1 | 10/2015 | Leimbach et al. | |
| 2016/0310134 A1 | 10/2016 | Contini et al. | |
| 2017/0007244 A1 | 1/2017 | Shelton, IV et al. | |
| 2017/0086823 A1 | 3/2017 | Leimbach et al. | |

OTHER PUBLICATIONS

U.S. Appl. No. 15/634,418, filed Jun. 27, 2017.
U.S. Appl. No. 15/634,452, filed Jun. 27, 2017.
U.S. Appl. No. 15/634,475, filed Jun. 27, 2017.
U.S. Appl. No. 15/634,497, filed Jun. 27, 2017.
U.S. Appl. No. 15/634,524, filed Jun. 27, 2017.
U.S. Appl. No. 15/634,556, filed Jun. 27, 2017.
U.S. Appl. No. 15/634,589, filed Jun. 27, 2017.
U.S. Appl. No. 15/634,620, filed Jun. 27, 2017.
European Search Report and Written Opinion dated Nov. 16, 2018 for Application No. EP 18180162.2, 11 pgs.
International Search Report and Written Opinion dated Aug. 28, 2018 for Application No. PCT/IB2018/053668, 14 pgs.

* cited by examiner

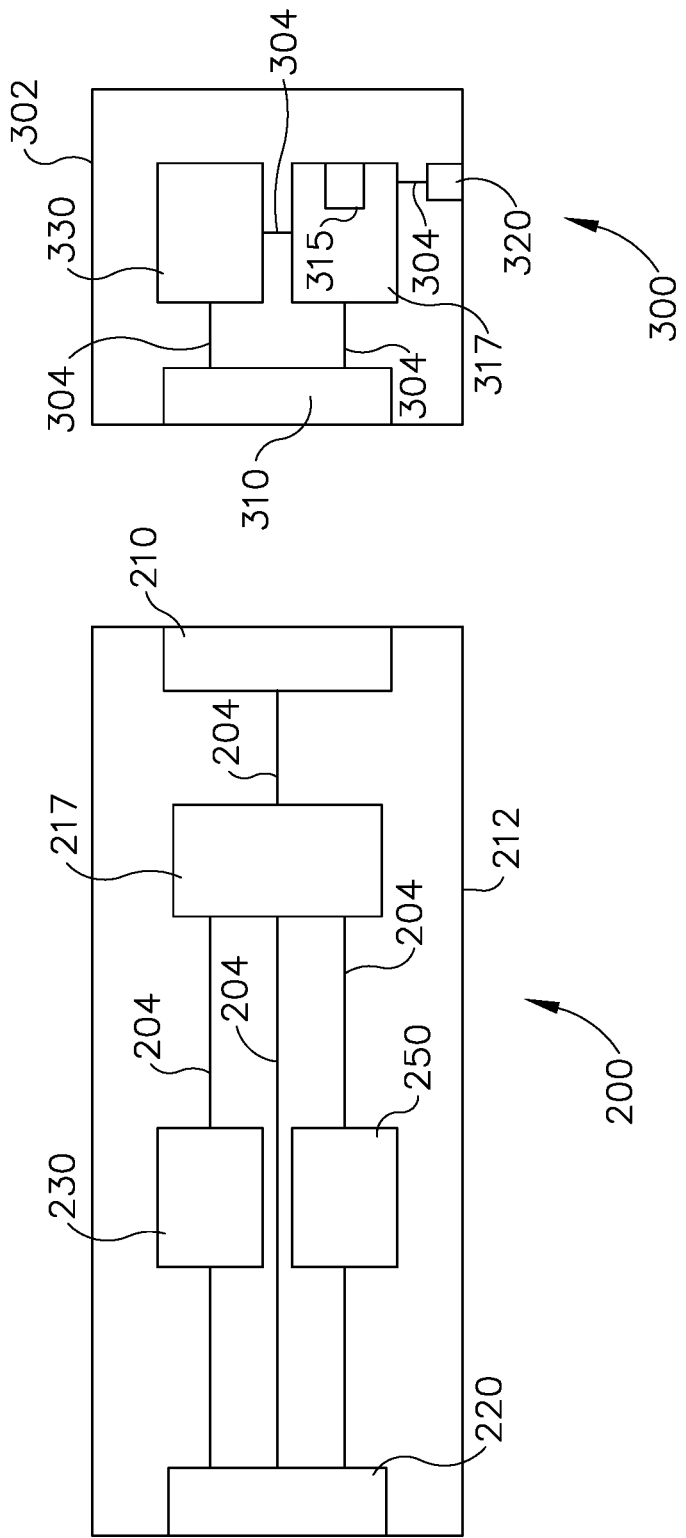

BATTERY PACK WITH INTEGRATED CIRCUIT PROVIDING SLEEP MODE TO BATTERY PACK AND ASSOCIATED SURGICAL INSTRUMENT

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in various ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 7,000,818, entitled "Surgical Stapling Instrument Having Separate Distinct Closing and Firing Systems," issued Feb. 21, 2006; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

Examples of surgical staplers that may be particularly suited or use through a thoracotomy are disclosed in U.S. Patent Application Publication No. 2014/0243801, entitled "Surgical Instrument End Effector Articulation Drive with Pinion and Opposing Racks," published on Aug. 28, 2014; U.S. Patent Application Publication No. 2014/0239041, entitled "Lockout Feature for Movable Cutting Member of Surgical Instrument," Published Aug. 28, 2014; U.S. Patent Application Publication No. 2014/0239038, entitled "Surgical Instrument with Multi-Diameter Shaft," published Aug. 28, 2014; and U.S. Patent Application Publication No. 2014/0239044, entitled "installation Features for Surgical instrument End Effector Cartridge," published Aug. 28, 2014. The disclosure of each of the above-cited U.S. Patent Applications is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 7A depicts a schematic view of an exemplary alternative handle assembly and an exemplary alternative battery pack that may be readily incorporated into the surgical instrument of FIG. 1, where the handle assembly and the battery pack are decoupled from each other;

Figure 1:
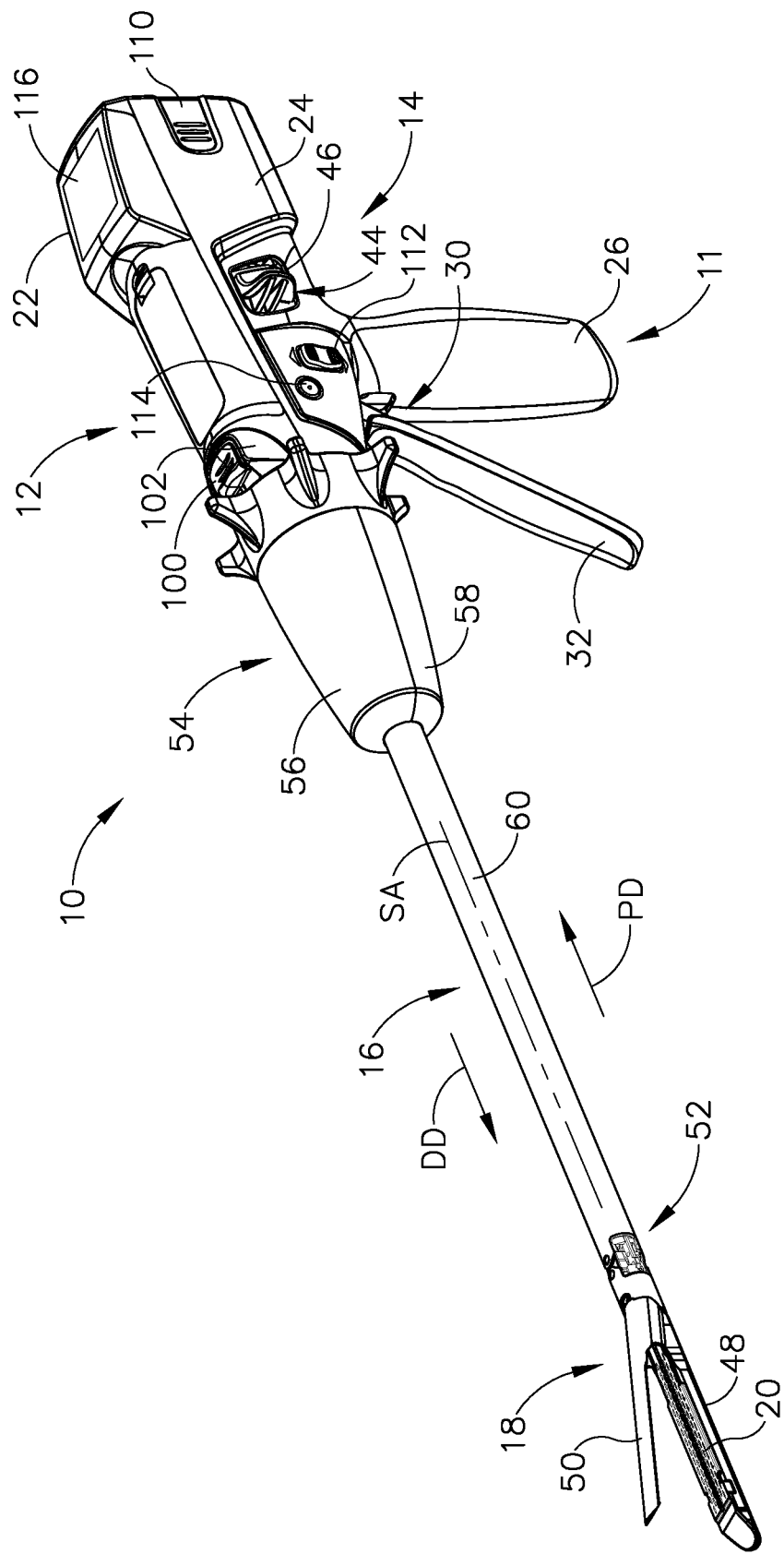
FIG. 1 depicts a perspective view of an exemplary surgical instrument including an interchangeable shaft assembly and a handle assembly.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to an operator or other operator grasping a surgical instrument having a distal surgical end effector. The term "proximal" refers the position of an element closer to the operator or other operator and the term "distal" refers to the position of an element closer to the surgical end effector of the surgical instrument and further away from the operator or other operator. Although the surgical instruments described herein comprise motorized implements for cutting and stapling, it will be appreciated that the configurations described herein may be used with any suitable type of electrical surgical instrument such as cutters, claspers, staplers, RF cutter/coagulators, ultrasonic cutter/coagulators, and laser cutter/coagulators, for example.

I. Overview of Exemplary Surgical Instrument

FIG. 1 depicts a motor-driven surgical cutting and fastening instrument (10) that includes a handle assembly (11) and a removable shaft assembly (16). In some versions, handle assembly (11) and shaft assembly (16) are each provided a single-use, disposable components. In some other versions, handle assembly (11) and shaft assembly (16) are each provided as reusable components. As another merely illustrative example, shaft assembly (16) may be provided as a single-use, disposable component while handle assembly is provided as a reusable component. Various suitable ways in which reusable versions of handle assembly (11) and shaft assembly (16) may be suitable reprocessed for reuse will be apparent to those of ordinary skill in the art in view of the teachings herein.

Handle assembly (11) of the present example includes a housing (12), a closure trigger (32), and a firing trigger (33). At least a portion of housing (12) forms a handle (14) that is configured to be grasped, manipulated and actuated by the clinician. Housing (12) is configured for operative attachment to shaft assembly (16), which has a surgical end effector (18) operatively coupled thereto. As described below, end effector (18) is configured to perform one or more surgical tasks or procedures. In particular, end effector (18) of the example shown in FIG. 1 is operable to perform a surgical cutting and stapling procedure, in a manner similar to an end effector of a conventional endocutter, though it should be understood that this is just one merely illustrative example.

Figure 2:
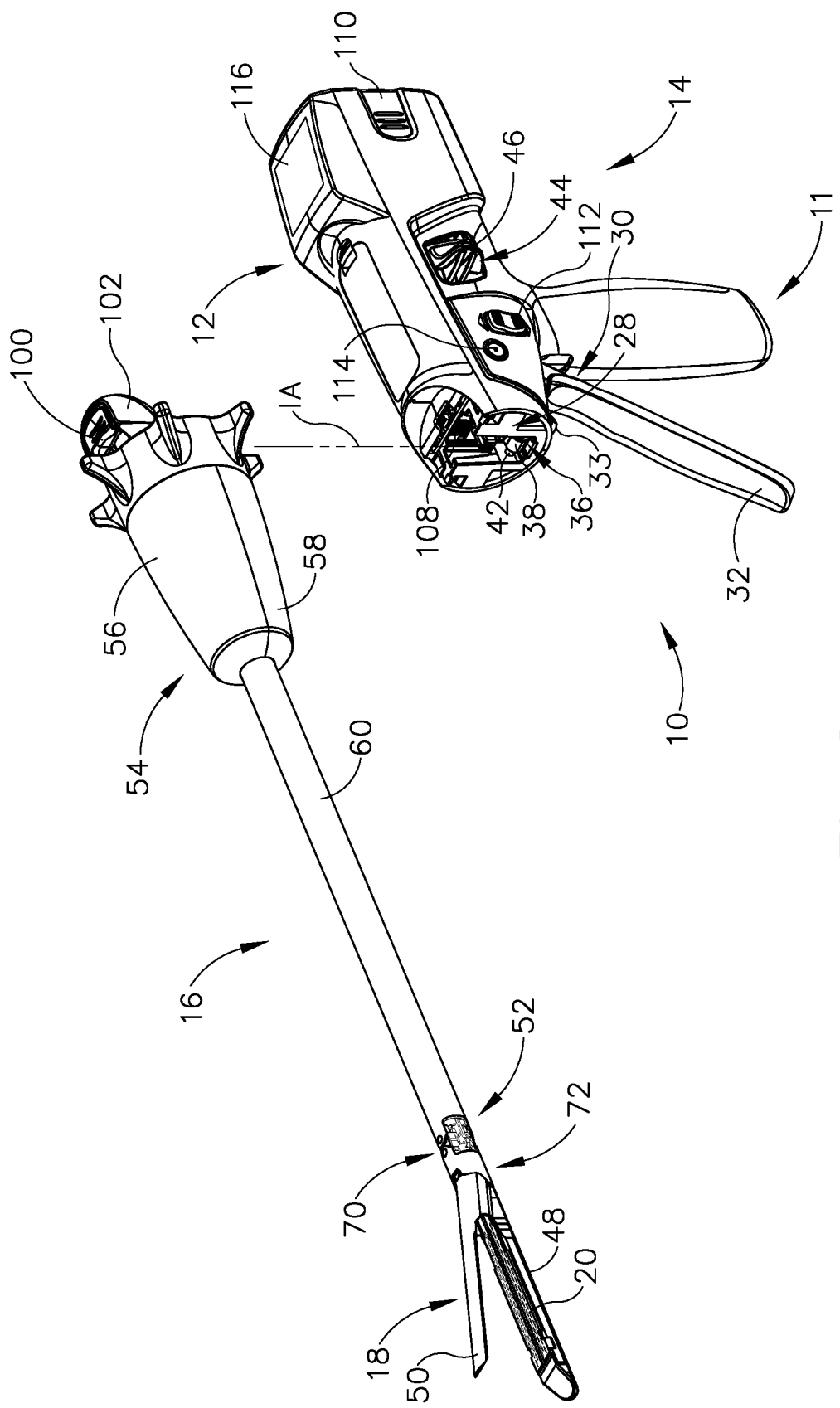
FIG. 2 depicts a perspective view of the instrument of FIG. 1, showing the shaft assembly disassembled from the handle assembly of the instrument.
Figure 3:
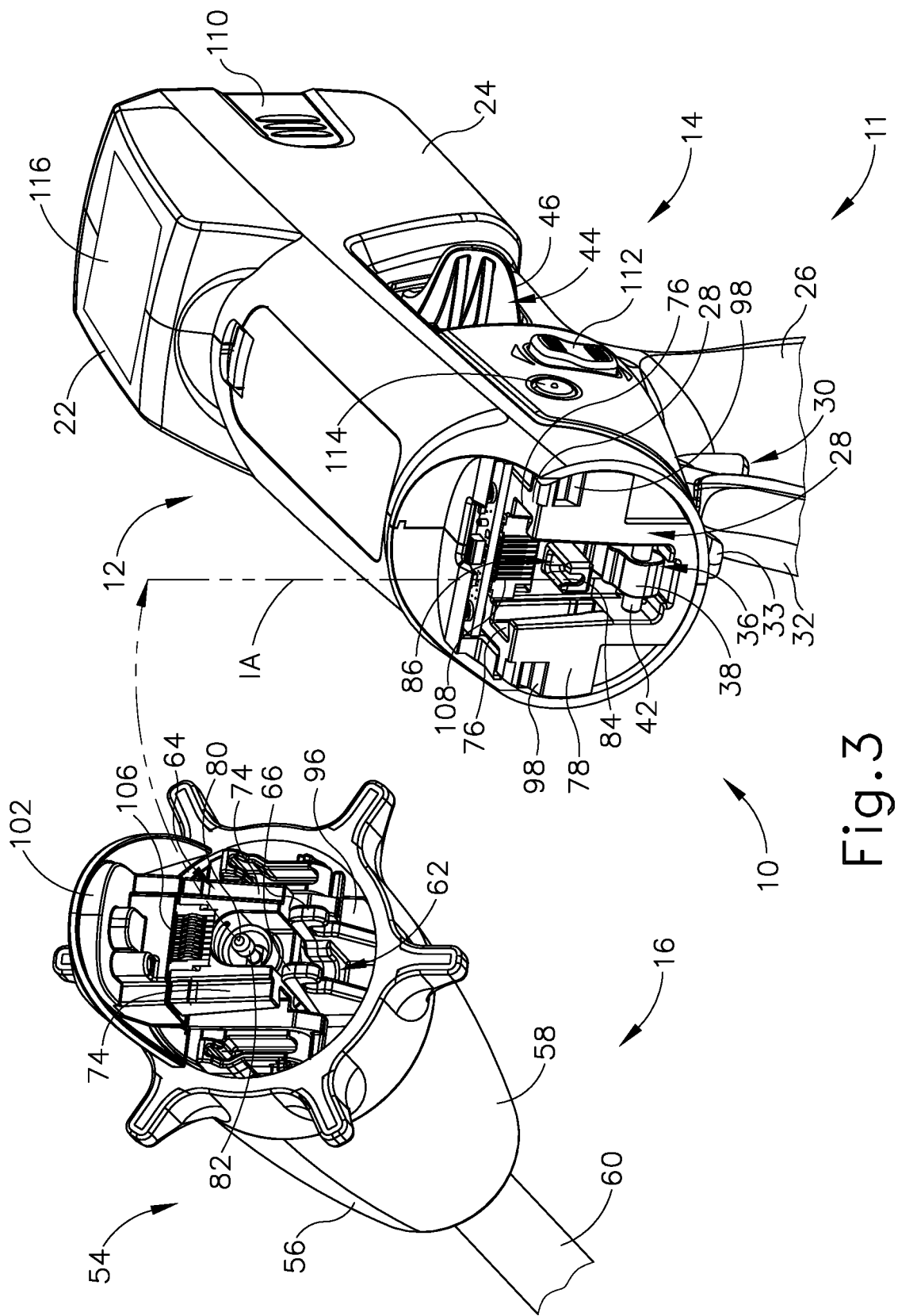
FIG. 3 depicts a partial perspective view of the instrument of FIG. 1, showing the shaft assembly disassembled from the handle assembly of the instrument.

FIG. 1 illustrates surgical instrument (10) with interchangeable shaft assembly (16) operatively coupled to handle assembly (11). FIGS. 2-3 illustrate attachment of interchangeable shaft assembly (16) to housing (12) of handle (14). Handle (14) includes a pair of interconnectable handle housing segments (22, 24) that may be interconnected by screws, snap features, adhesive, etc. In the illustrated arrangement, handle housing segments (22, 24) cooperate to form a pistol grip portion (26) that can be grasped and manipulated by the clinician. As will be discussed in further detail below, handle (14) operatively supports a plurality of drive systems therein that are configured to generate and apply various control motions to corresponding portions of interchangeable shaft assembly (16) that is operatively attached thereto. As will also be discussed in further detail below, triggers (32, 33) are pivotable toward pistol grip portion (26) to activate at least some of the drive systems in handle (14).

Figure 5:
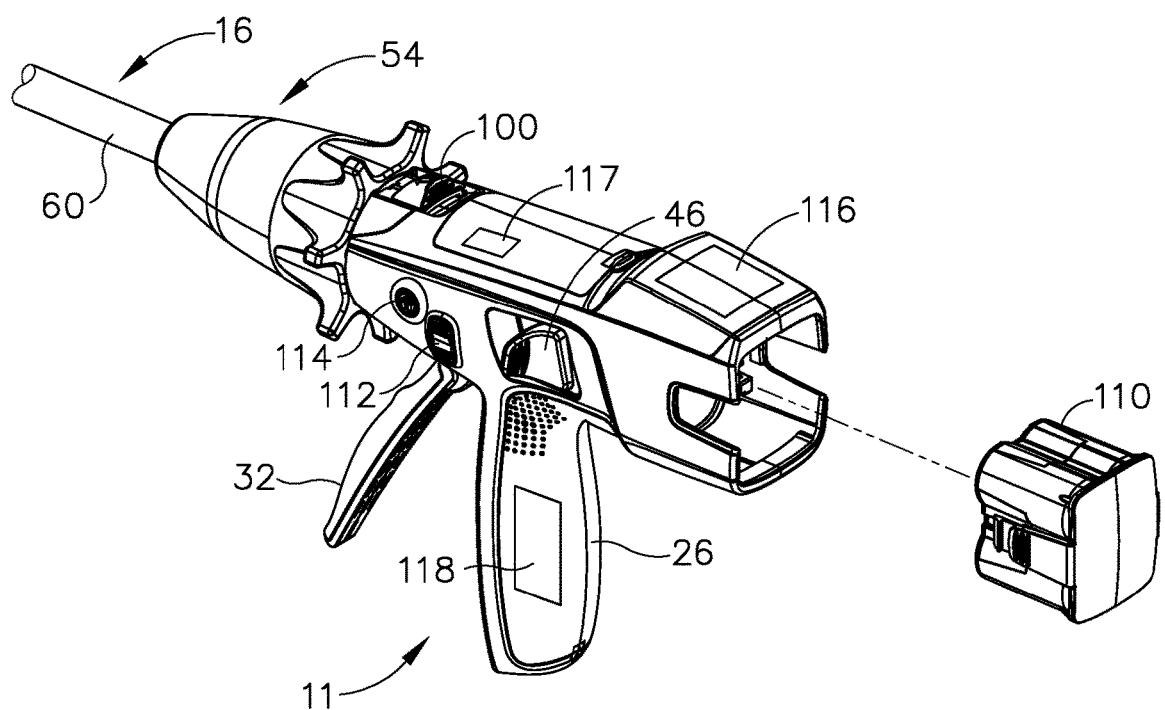
FIG. 5 depicts a perspective view of a proximal portion of the instrument of FIG. 1, with a battery removed from the handle assembly.

At least some of the drive systems in handle assembly (11) are ultimately driven by a motor (118), which is shown schematically in FIG. 5. In the present example, motor (118) is located in pistol grip portion (26), though it should be understood that motor (118) may be located at any other suitable position. Motor (118) receives power from a battery pack (110), which is secured to handle (14). In the present example, and as shown in FIG. 5, battery pack (110) is removable from handle (14). In some other versions, battery pack (110) is not removable from handle (14). In some such versions, battery pack (110) (or a variation thereof) is fully contained within handle housing segments (22, 24). Various suitable forms that motor (118) and battery pack (110) may take will be apparent to those of ordinary skill in the art in view of the teachings herein.

As also shown schematically in FIG. 5, a control circuit (117) is contained within handle (14). By way of example only, control circuit (117) may comprise a microcontroller and/or various other components as will be apparent to those of ordinary skill in the art in view of the teachings herein. Control circuit (117) is configured to store and execute control algorithms to drive motor (118). Control circuit (117) is also configured to drive a graphical user interface (116), which is located at the proximal end of handle assembly (11). In some versions, control circuit (117) is configured to receive and process one or more signals from shaft assembly (16). By way of example only, control circuit (117) may be configured and operable in accordance with at least some of the teachings of U.S. Pub. No. 2015/0272575, entitled "Surgical instrument Comprising a Sensor System,"

published Oct. 1, 2015, the disclosure of which is incorporated by reference herein. Other suitable ways in which control circuit (117) may be configured and operable will be apparent to those of ordinary skill in the art in view of the teachings herein.

As best seen in FIG. 3, a frame (28) of handle (14) operatively supports a plurality of drive systems. In this particular example, frame (28) operatively supports a "first" or closure drive system, generally designated as (30), which may be employed to apply closing and opening motions to interchangeable shaft assembly (16) that is operatively attached or coupled thereto. Also in this particular example, closure drive system (30) includes an actuator in the form of a closure trigger (32) that is pivotally supported by frame (28). More specifically, closure trigger (32) is pivotally coupled to housing (14) by a pin (not shown). Such arrangement enables closure trigger (32) to be manipulated by a clinician such that when the clinician grasps pistol grip portion (26) of handle (14), closure trigger (32) may be easily pivoted from a starting or "unactuated" position (FIG. 4A) toward pistol grip portion (26) to an "actuated" position; and more particularly to a fully compressed or fully actuated position (FIG. 4B). Closure trigger (32) may be biased into the unactuated position by spring or other biasing arrangement (not shown).

In the present example, closure drive system (30) further includes a closure linkage assembly (36) pivotally coupled to closure trigger (32). A portion of closure linkage assembly (36) is shown in FIG. 3. Closure linkage assembly (36) may include a first closure link (not shown) and a second closure link (38) that are pivotally coupled to closure trigger (32) by a pin (not shown). Second closure link (38) may also be referred to herein as an "attachment member" and includes a transverse attachment pin (42). As shown in FIG. 3, attachment pin (42) is exposed when shaft assembly (16) is detached from handle assembly (11). Attachment pin (42) may thus couple with a complementary feature of a shaft assembly (16) when shaft assembly (16) is coupled with handle assembly (11), as described in greater detail below.

Still referring to FIGS. 1-3, first closure link (not shown) is configured to cooperate with a closure release assembly (44) that is pivotally coupled to frame (28). In at least one example, closure release assembly (44) has a release button assembly (46) with a distally protruding locking pawl (not shown) formed thereon. Release button assembly (46) may be pivoted in a counterclockwise direction by a release spring (not shown). As the clinician depresses closure trigger (32) from its unactuated position toward pistol grip portion (26) of handle (14), first closure link (not shown) pivots upwardly to a point where a locking pawl (not shown) drops into retaining engagement with first closure link (not shown), thereby preventing closure trigger (32) from returning to the unactuated position. Thus, closure release assembly (44) serves to lock closure trigger (32) in the fully actuated position.

When the clinician desires to unlock closure trigger (32) from the actuated position to return to the unactuated position, the clinician simply pivots closure release button assembly (46) by urging release button assembly (46) distally, such that locking pawl (not shown) is moved out of engagement with the first closure link (not shown). When the locking pawl (not shown) has been moved out of engagement with first closure link (not shown), closure trigger (32) may return back to the unactuated position in response to a resilient bias urging closure trigger (32) back to the unactuated position. Other closure trigger locking and release arrangements may also be employed.

Interchangeable shaft assembly (16) further includes an articulation joint (52) and an articulation lock (not shown) that can be configured to releasably hold end effector (18) in a desired position relative to a longitudinal axis of shaft assembly (16). In the present example, articulation joint (52) is configured to allow end effector (18) to be laterally deflected away from the longitudinal axis of shaft assembly (16), as is known in the art. By way of example only, end effector (18), articulation joint (52), and the articulation lock (not shown) may be configured and operable in accordance with at least some of the teachings of U.S. Pub. No. 2014/0263541, entitled "Articulatable Surgical Instrument Comprising an Articulation Lock," published Sep. 18, 2014.

In the present example, articulation at articulation joint (52) is motorized via motor (118), based on control input from the operator via an articulation control rocker (112) on handle assembly (11). By way of example only, when the operator presses on the upper portion of articulation control rocker (112), end effector (18) may laterally pivot to the right (viewing instrument (10) from above) at articulation joint (52); and when the operator presses on the lower portion of articulation control rocker (112), end effector (18) may laterally pivot to the left (viewing instrument (10) from above) at articulation joint (52). In some versions, the other side of handle assembly (11) includes another articulation control rocker (112). In such versions, the articulation control rocker (112) on the other side of handle assembly (11) may be configured to provide pivoting of end effector (18) in directions opposite to those listed above in response to upper actuation of articulation control rocker (112) and lower actuation of articulation control rocker (112). By way of example only, articulation control rocker (112) and the rest of the features that provide motorized articulation of end effector (18) at articulation joint (52) may be configured and operable in accordance with at least some of the teachings of U.S. Pub. No. 2015/0280384, entitled "Surgical instrument Comprising a Rotatable Shaft," published Oct. 1, 2015, the disclosure of which is incorporated by reference herein. Other suitable ways in which articulation control rocker (112) and the rest of the features that provide motorized articulation of end effector (18) at articulation joint (52) may be configured and operable will be apparent to those of ordinary skill in the art in view of the teachings herein.

End effector (18) of the present example comprises a lower jaw in the form of an elongated channel (48) that is configured to operatively a support staple cartridge (20) therein. End effector (18) of the present example further includes an upper jaw in the form of an anvil (50) that is pivotally supported relative to elongated channel (48). Interchangeable shaft assembly (16) further includes a proximal housing or nozzle (54) comprised of nozzle portions (56, 58); and a closure tube (60) that can be utilized to close and/or open anvil (50) of end effector (18). Shaft assembly (16) also includes a closure shuttle (62) that is slidably supported within a chassis (64) of shaft assembly (16) such that closure shuttle (62) may be axially moved relative to chassis (64). Closure shuttle (62) includes a pair of proximally-protruding hooks (66) that are configured for attachment to attachment pin (42) that is attached to second closure link (38). A proximal end (not shown) of closure tube (60) is coupled to closure shuttle (62) for relative rotation thereto, though the coupling of closure tube (60) with closure shuttle (62) provides that closure tube (60) and closure shuttle (62) will translate longitudinally with each other. A closure spring (not shown) is journaled on closure tube (60) and serves to bias closure tube (60) in the proximal direction (PD), which can serve to pivot closure trigger (32)

into the unactuated position when shaft assembly (16) is operatively coupled to handle (14).

In the present example, articulation joint (52) includes a double pivot closure sleeve assembly (70). Double pivot closure sleeve assembly (70) includes an end effector closure sleeve assembly (72) for engaging an opening tab on anvil (50) in the various manners described in U.S. Pub. No. 2014/0263541, the disclosure of which is incorporated by reference herein. It should be understood that double pivot closure sleeve assembly (70) is coupled with closure tube (60) such that double pivot closure sleeve assembly (70) translates with closure tube (60) in response to pivotal movement of closure trigger (32), even when articulation joint (52) is in an articulated state (i.e., when end effector (18) is pivotally deflected laterally away from the longitudinal axis of shaft assembly (16) at articulation joint (52)). Moreover, the engagement of end effector closure sleeve assembly (72) with anvil (50) provides pivotal movement of anvil (50) toward staple cartridge (20) in response to distal translation of double pivot closure sleeve assembly (70) and closure tube (60); and pivotal movement of anvil (50) away from staple cartridge (20) in response to proximal translation of double pivot closure sleeve assembly (70) and closure tube (60). While shaft assembly (16) of the present example includes articulation joint (52), other interchangeable shaft assemblies may lack articulation capabilities.

As shown in FIG. 3, chassis (64) includes a pair of tapered attachment portions (74) formed thereon that are adapted to be received within corresponding dovetail slots (76) formed within a distal attachment flange portion (78) of frame (28). Each dovetail slot (76) may be tapered or generally V-shaped to seatingly receive attachment portions (74) therein. A shaft attachment lug (80) is formed on the proximal end of an intermediate firing shaft (82). Thus, when interchangeable shaft assembly (16) is coupled to handle (14), shaft attachment lug (80) is received in a firing shaft attachment cradle (84) formed in a distal end of a longitudinal drive member (86). When shaft attachment lug (80) is received in firing shaft attachment cradle (84), intermediate firing shaft (82) will translate longitudinally with longitudinal drive member (86). When intermediate firing shaft (82) translates distally, intermediate firing shaft (82) actuates end effector (18) to drive staples into tissue and cut the tissue, as is known in the art. By way of example only, this actuation of end effector (18) may be carried out in accordance with at least some of the teachings of U.S. Pub. No. 2015/0280384, the disclosure of which is incorporated by reference herein; and/or in accordance with the teachings of various other references cited herein.

Figure 4A:
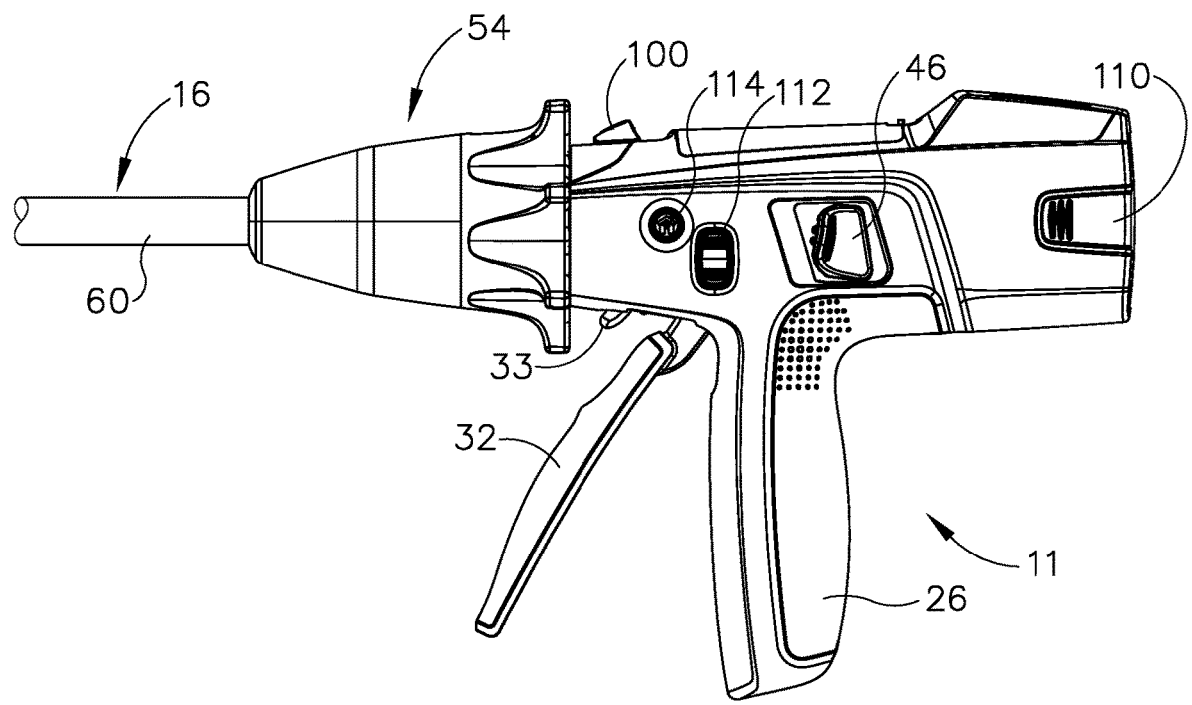
FIG. 4A depicts a side elevational view of a proximal portion of the instrument of FIG. 1, with a closure trigger in a first pivotal position and a firing trigger in a first pivotal position.
Figure 4B:
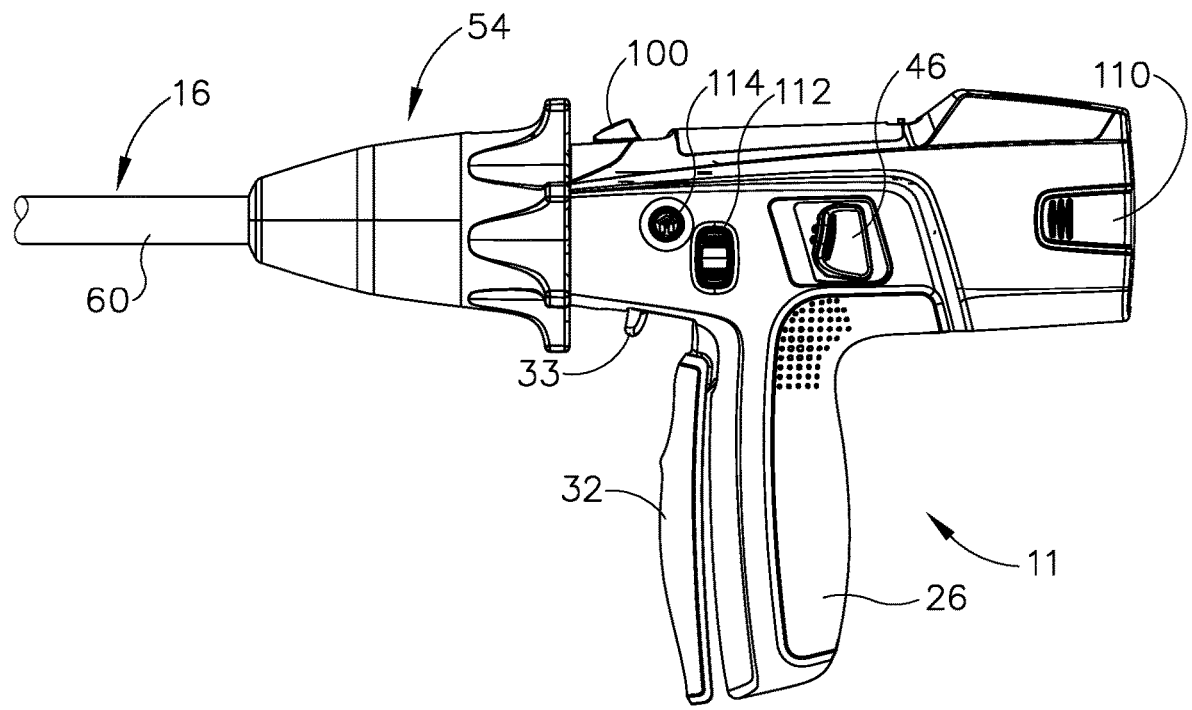
FIG. 4B depicts a side elevational view of a proximal portion of the instrument of FIG. 1, with the closure trigger in a second pivotal position and the firing trigger in a second pivotal position.
Figure 4C:
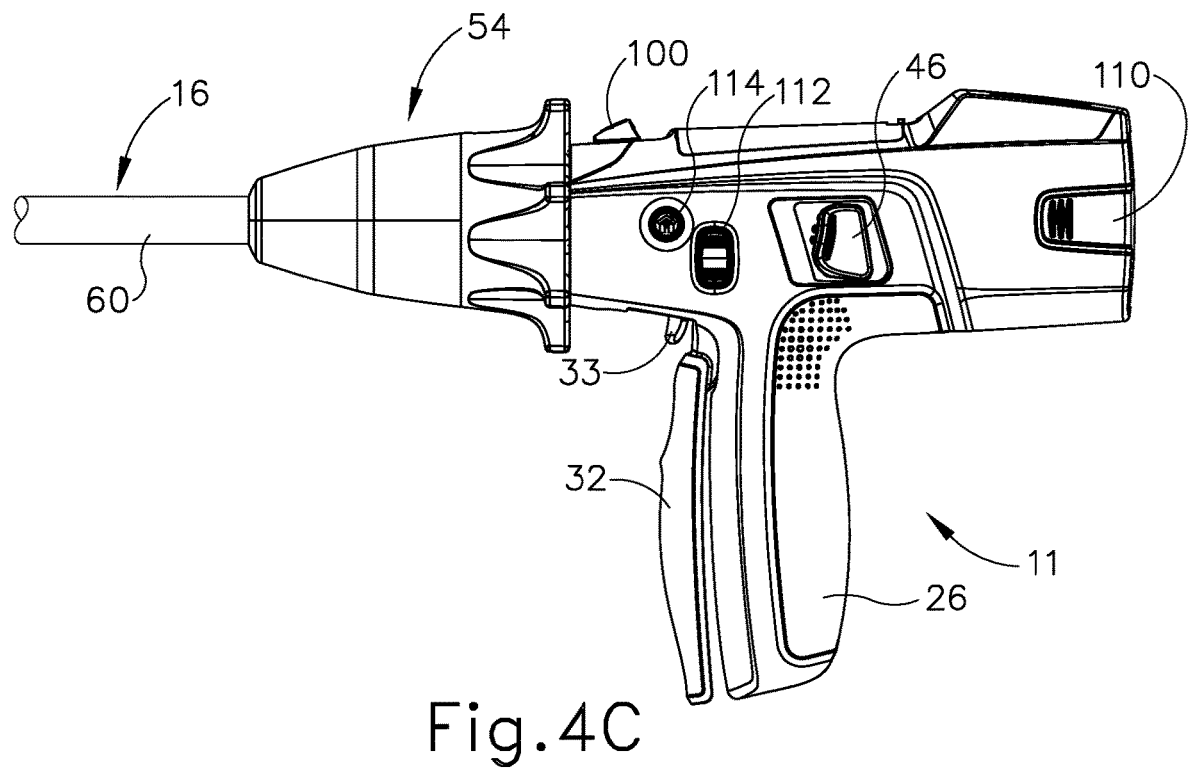
FIG. 4C depicts a side elevational view of a proximal portion of the instrument of FIG. 1, with the closure trigger in the second pivotal position and the firing trigger in a third pivotal position.

FIGS. 4A-4C show the different states of handle assembly (11) during the different states of actuation of end effector (18). In FIG. 4A, handle assembly (11) is in a state where closure trigger (32) is in a non-actuated pivotal position and firing trigger (33) is in a non-actuated pivotal position. At this stage, end effector (18) is in an opened state where anvil (50) is pivoted away from staple cartridge (20).

In FIG. 4B, handle assembly (11) is in a state where closure trigger (32) is in an actuated pivotal position. As noted above, closure trigger (32) will be locked in this position until the operator actuates release button assembly (46). At this stage, end effector is in a closed but unfired state where anvil (50) is pivoted toward staple cartridge (20), such that tissue is being compressed between anvil (50) and cartridge (20). However, firing shaft (82) has not yet been driven distally to actuate staples from staple cartridge (20), and the knife at the distal end of firing shaft (82) has not yet severed the tissue between anvil (20) and staple cartridge (20). It should be noted that firing trigger (33) is in a partially-actuated pivotal position in FIG. 4B, due to the travel of closure trigger (32) from the non-actuated pivotal position to the actuated pivotal position. However, this movement of firing trigger (33) is only provided in order to improve access to firing trigger (33) for the operator. In other words, this movement of firing trigger (33) from the position shown in FIG. 4A to the position shown in FIG. 4B does not yet activate a firing sequence.

In FIG. 4C, handle assembly is in a state where closure trigger (32) remains in the actuated pivotal position, and firing trigger (33) has been pivoted to an actuated pivotal position. This actuation of firing trigger (33) activates motor (118) to drive longitudinal drive member (86) longitudinally, which in turn drives firing shaft (82) longitudinally. The longitudinal movement of thing shaft (82) results in actuation of staples from staple cartridge (20) into the tissue compressed between anvil (50) and staple cartridge (20); and further results in the severing of the tissue compressed between anvil (50) and staple cartridge (20). In some versions, an additional safety trigger is provided. For instance, the additional safety trigger may prevent actuation of firing trigger (33) until the safety trigger is actuated. In other words, after reaching the state shown in FIG. 4B, when the operator is ready to actuate firing trigger (33), the operator must first actuate the safety trigger and then actuate firing trigger (33). It should be understood that the presence of a safety trigger may prevent inadvertent actuation of firing trigger (33).

It should also be understood that, in the present example, the actuation of anvil (50) toward staple cartridge (20) is provided through purely mechanical couplings between closure trigger (32) and anvil (50), such that motor (118) is not used to actuate anvil (50). It should also be understood that, in the present example, the actuation of firing shaft (82) (and, hence, the actuation of staple cartridge (20)) is provided through activation of motor (118). In addition, the actuation of articulation joint (52) is provided through activation of motor (118) in the present example. This motorized actuation of articulation joint (52) is provided via longitudinal translation of drive member (86). A clutch assembly (not shown) within shaft assembly (16) is operable to selectively couple longitudinal translation of drive member (86) with features to either drive articulation joint (52) or actuate staple cartridge (20). Such selective coupling via the clutch assembly is based on the pivotal position of closure trigger (32). In particular, when closure trigger (32) is in the non-actuated position shown in FIG. 4A, activation of motor (118) (in response to activation of articulation control rocker (112)) will drive articulation joint (52). When closure trigger (32) is in the actuated position shown in FIG. 4B, activation of motor (118) (in response to actuation of firing trigger (33)) will actuate staple cartridge (20). By way of example only, the clutch assembly may be configured and operable in accordance with at least some of the teachings of U.S. Pub. No. 2015/0280384, the disclosure of which is incorporated by reference herein.

In the present example, handle assembly (11) also includes a "home" button (114). By way of example only, when anvil (50) is in a closed position, "home" button (114) may be operable to activate motor (118) to retract drive member (86) proximally to a proximal-most, "home" position. In addition, or in the alternative, when anvil (50) is in an open position, "home" button (114) may be operable to activate motor (118) to drive articulation joint (52) to achieve a non-articulated state, such that end effector (18) is coaxially aligned with shaft assembly (16). In addition, or in the alternative, "home" button (114) may activate graphical user interface (116) to return to a "home" screen. Other suitable operations that may be provided in response to activation of "home" button (114) will be apparent to those of ordinary skill in the art in view of the teachings herein.

Shaft assembly (16) of the present example further includes a latch system for removably coupling shaft assembly (16) to handle assembly (11) and, more specifically, to frame (28). By way of example only, this latch system may include a lock yoke or other kind of lock member that is movably coupled to chassis (64). As shown in FIG. 3, such a lock yoke may include two proximally protruding lock lugs (96) that are configured for releasable engagement with corresponding lock detents or grooves (98) in frame (28). In some versions, the lock yoke is biased in the proximal direction by a resilient member (e.g., a spring, etc.). Actuation of the lock yoke may be accomplished by a latch button (100) that is slidably mounted on a latch actuator assembly (102) that is mounted to chassis (64). Latch button (100) may be biased in a proximal direction relative to the lock yoke. The lock yoke may be moved to an unlocked position by urging latch button (100) the in distal direction, which also causes the lock yoke to pivot out of retaining engagement with frame (28). When the lock yoke is in "retaining engagement" with frame (28), lock lugs (96) are retainingly seated within the corresponding lock detents or grooves (98). By way of further example only, shaft assembly (16) may be removably coupled with handle assembly (11) in accordance with at least some of the teachings of U.S. Pub. No. 2017/0086823, entitled "Surgical Stapling Instrument with Shaft Release, Powered Firing, and Powered Articulation," published Mar. 30, 2017, the disclosure of which is incorporated by reference herein; in accordance with at least some of the teachings of U.S. Pub. No. 2015/0280384, the disclosure of which is incorporated by reference herein; and/or in any other suitable fashion.

To commence the coupling process between shaft assembly (16) and handle assembly (11), the clinician may position chassis (64) of interchangeable shaft assembly (16) above or adjacent to frame (28) such that tapered attachment portions (74) formed on chassis (64) are aligned with dovetail slots (76) in frame (28). The clinician may then move shaft assembly (16) along an installation axis (IA) that is perpendicular to the longitudinal axis of shaft assembly (16) to seat attachment portions (74) in "operative engagement" with the corresponding dovetail receiving slots (76). In doing so, shaft attachment lug (80) on intermediate firing shaft (82) will also be seated in cradle (84) in the longitudinally movable drive member (86) and the portions of pin (42) on second closure link (38) will be seated in the corresponding hooks (66) in closure shuttle (62). As used herein, the term "operative engagement" in the context of two components means that the two components are sufficiently engaged with each other so that upon application of an actuation motion thereto, the components may carry out their intended action, function, and/or procedure.

As discussed above, at least five systems of interchangeable shaft assembly (16) may be operatively coupled with at least five corresponding systems of handle (14). A first system comprises a frame system that couples and/or aligns the frame or spine of shaft assembly (16) with frame (28) of the handle (14). A second system is the latch system that releasably locks the shaft assembly (16) to the handle (14).

A third system is closure drive system (30) that may operatively connect closure trigger (32) of handle (14) and closure tube (60) and anvil (50) of shaft assembly (16). As outlined above, closure shuttle (62) of shaft assembly (16) engages with pin (42) on second closure link (38). Through closure drive system (30), anvil (50) pivots toward and away from staple cartridge (20) based on pivotal movement of closure trigger (32) toward and away from pistol grip (26).

A fourth system is an articulation and firing drive system operatively connecting firing trigger (33) of handle (14) with intermediate firing shaft (82) of the shaft assembly (16). As outlined above, the shaft attachment lug (80) operatively connects with the cradle (84) of the longitudinal drive member (86). This fourth system provides motorized actuation of either articulation joint (52) or staple cartridge (20), depending on the pivotal position of closure trigger (32). When closure trigger (32) is in a non-actuated pivotal position, the fourth system operatively connects articulation control rocker (112) with articulation joint (52), thereby providing motorized pivotal deflection of end effector (18) toward and away from the longitudinal axis of shaft assembly (11) at articulation joint (52). When closure trigger (32) is in an actuated pivotal position, the fourth system operatively connects firing trigger (33) with staple cartridge (20), resulting in stapling and cutting of tissue captured between anvil (50) and staple cartridge (20) in response to actuation of firing trigger (33).

A fifth system is an electrical system that can signal to control circuit (117) in handle (14) that the shaft assembly (16) has been operatively engaged with the handle (14), to conduct power and/or communicate signals between the shaft assembly (16) and the handle (14). In the present example, and as shown in FIG. 3, shaft assembly (16) includes an electrical connector (106) that is operatively mounted to a shaft circuit board (not shown). Electrical connector (106) is configured for mating engagement with a corresponding electrical connector (108) on a handle control board (not shown). Further details regarding the circuitry and control systems may be found in U.S. Pub. No. 2014/0263541, the disclosure of which is incorporated by reference herein and/or U.S. Pub. No. 2015/0272575, the disclosure of which is incorporated by reference herein.

Other kinds of systems of interchangeable shaft assembly (16) that may be operatively coupled with at corresponding systems of the handle (14) will be apparent to those of ordinary skill in the art in view of the teachings herein.

As noted above, handle assembly (11) of the present example includes a graphical user interface (116). By way of example only, graphical user interface (116) may be used to display various information about the operational state of battery (110), the operational state of end effector (18), the operational state of articulation joint (52), the operational state of triggers (32, 33), and/or any other kinds of information. Other suitable kinds of information that may be displayed via graphical user interface will be apparent to those of ordinary skill in the art in view of the teachings herein.

Figure 6:
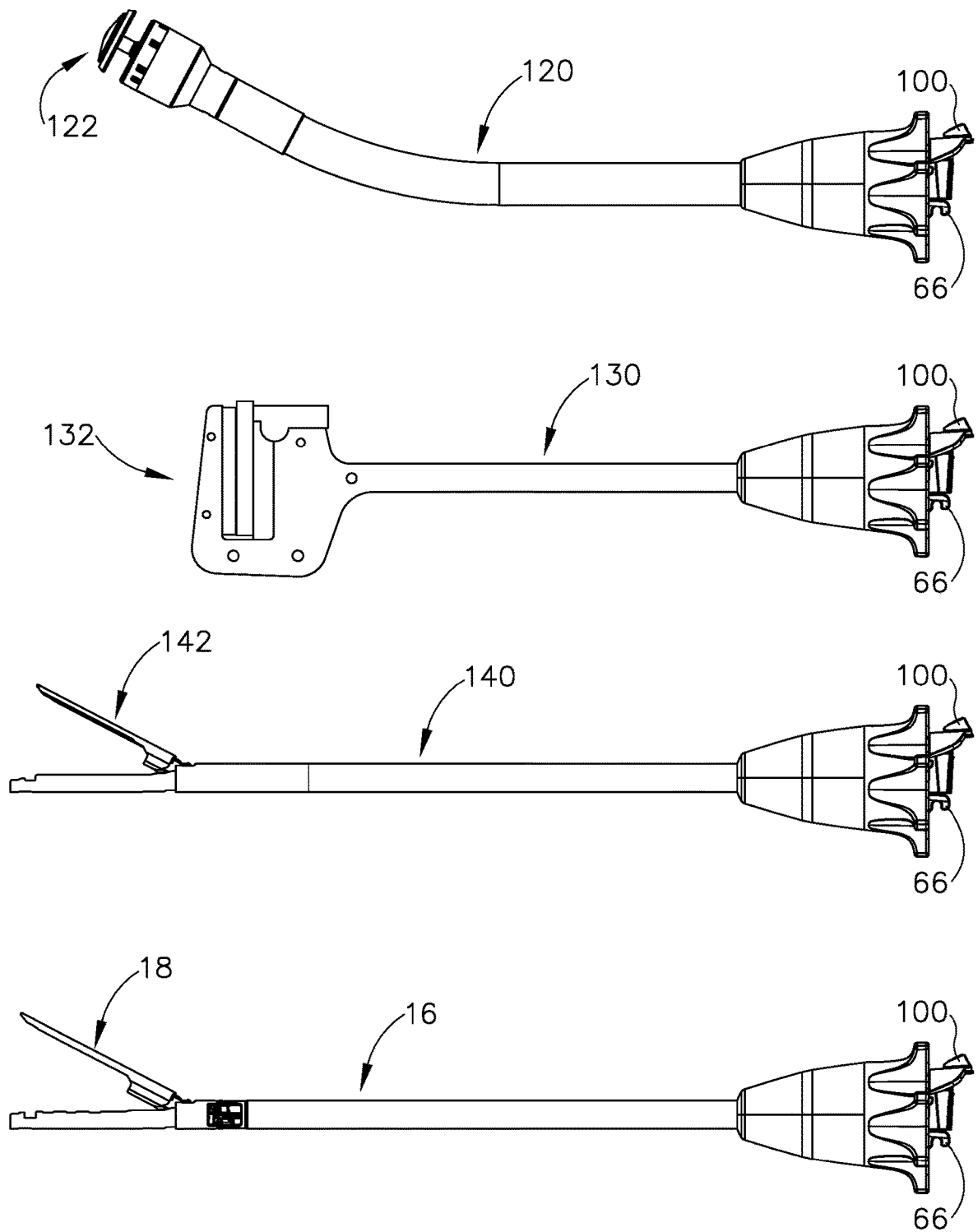
FIG. 6 depicts a side elevational view of an array of alternative shaft assemblies that may be used with the instrument of FIG. 1.

Handle assembly (11) may be configured for use in connection with interchangeable shaft assemblies that include end effectors that are adapted to support different sizes and types of staple cartridges, have different shaft lengths, sizes, and types, etc. By way of example only, FIG. 6 shows various different kinds of shaft assemblies (16, 120, 130, 140) that may be used with handle assembly (11). In particular, FIG. 6 shows a circular stapler shaft assembly (120) with an end effector (122) that is operable to perform a circular stapling operation (e.g., end-to-end anastomosis); a liner stapler shaft assembly (130) with an end effector (132) that is operable to perform a linear stapling operation; and a second endocutter shaft assembly (140) with an end effector (142) that is operable to perform the same kind of stapling and cutting operation as end effector (18). However, in this example, shaft assembly (140) is shorter than shaft assembly (16), shaft assembly (140) has a smaller diameter than shaft assembly (16), and end effector (142) is smaller than end effector (18). It should be understood that these various surgical stapling shaft assemblies (16, 120, 130, 140) are merely illustrative examples.

It should also be understood that control circuit (117) may be configured to detect the kind of shaft assembly (16, 120, 130, 140) coupled with handle assembly (11), and select a control algorithm suited for that particular kind of shaft assembly (16, 120, 130, 140). As another merely illustrative example, each shaft assembly (16, 120, 130, 140) may have a chip or other memory device storing the control algorithm suited for that particular kind of shaft assembly (16, 120, 130, 140); and control circuit (117) may receive and execute that control algorithm after shaft assembly (16, 120, 130, 140) is coupled with handle assembly (11).

In addition, handle assembly (11) may also be effectively employed with a variety of other interchangeable shaft assemblies including those assemblies that are configured to apply other motions and kinds of energy such as, for example, radio frequency (RF) energy, ultrasonic energy and/or motion to end effector arrangements adapted for use in connection with various surgical applications and procedures. Furthermore, end effectors, shaft assemblies, handles, surgical instruments, and/or surgical instrument systems can utilize any suitable fastener, or fasteners, to fasten tissue. For instance, a fastener cartridge comprising a plurality of fasteners removably stored therein can be removably inserted into and/or attached to the end effector of a shaft assembly. Various examples of such cartridges are disclosed in various references that are cited herein.

The various shaft assemblies (16) disclosed herein may employ sensors and various other components that require electrical communication with control circuit (117) in handled assembly (11). The electrical communications may be provided via mating electrical connectors (106, 108). By way of example only, such sensors and other components may be constructed and operable in accordance with at least some of the teachings of U.S. Pub. No. 2015/0272575, the disclosure of which is incorporated by reference herein. In addition or in the alternative, instrument (10) may be constructed and operable in accordance with at least some of the teachings of any of the various other references that are cited herein.

It will be appreciated that the various teachings herein may also be effectively employed in connection with robotically-controlled surgical systems. Thus, the term "housing" or "body" may also encompass a housing, body, or similar portion of a robotic system that houses or otherwise operatively supports at least one drive system that is configured to generate and apply at least one control motion which could be used to actuate the interchangeable shaft assemblies disclosed herein and their respective equivalents. The term "frame" may refer to a portion of a handheld surgical instrument. The term "frame" may also represent a portion of a robotically controlled surgical instrument and/or a portion of the robotic system that may be used to operatively control a surgical instrument. By way of example only, the interchangeable shaft assemblies disclosed herein may be employed with any of the various robotic systems, instruments, components and methods disclosed in U.S. Pat. No. 9,072,535, entitled "Surgical Stapling instruments with Rotatable Staple Deployment Arrangements," issued Jul. 7, 2015, the disclosure of which is incorporated by reference herein.

II. Surgical Instrument with Battery Pack having Independent Integrated Circuitry As noted above, handle assembly (11) includes battery pack (110), control circuit (117), first drive system (30) including closure trigger (32), and motor (118) configured to longitudinally drive intermediate firing shaft (82). Battery pack (110) is configured to power motor (118), while control circuit (117) is configured to store and execute control algorithms to drive motor (118). Depending on the pivotal position of closure trigger (32) of first drive system (30), motor (118) may be driven by control rocker (112) (the position shown in FIG. 4A), or firing trigger (33) (the position shown in FIGS. 4B-4C). Therefore, first drive system (30) may also be in communication with control circuit (117) such that control circuit (117) enables either control rocker (112) or firing trigger (33) to actuate motor (118).

Control circuit (117) may be configured to draw power from battery pack (110) such that control circuit (117) may perform the functions described above. Additionally, since control circuit (117) is configured to store and execute control algorithms to drive motor (118), control circuit (117) may instruct battery pack (110) when to power motor (118). Therefore, control circuit (117) may draw power from battery pack (110) to provide power to control circuit (117), motor (118), and other suitable components of handle assembly (11) such as graphical user interface (116).

Control circuit (117) may also be configured to enter and control a "sleep mode" for handle assembly (11). In sleep mode, control circuit (117) may stop performing some functions, such as powering graphic user interface (116) and motor (118), thereby draining less energy from battery pack (110) as compared to operation in a non-sleep mode. However, control circuit (117) may still drain some energy from battery pack (110) when control circuit (117) is in control of its own sleep mode. As one mere example, because control circuit (117) may control its own sleep mode, control circuit (117) may still drain some energy from battery pack (110) such that control circuit (117) may remain alert to the possibility of being fully reactivated in response to a general or specific user input, such as pressing home button (114) or control rocker (112).

Control circuit (117) may enter its own sleep mode for any suitable reason that would be apparent to one having ordinary skill in the art in view of the teachings herein. For example, if control circuit (117) does not receive any user input/instructions from various sources in a predetermined period of time, control circuit (117) may go into sleep mode. As another example, control circuit (117) may go into sleep mode in response to specific user input such as holding home button (114) for a predetermined amount of time. As yet another example, control circuit (117) may enter sleep mode in the absence of input from a motion sensor (e.g., accelerometer, etc.) after a predetermined duration of time.

Because control circuit (117) may unnecessarily drain energy stored within battery pack (110) when control circuit (117) enters and controls its own sleep mode, it may be beneficial to provide an alternative battery pack having its own independent circuitry that may function autonomously relative to control circuit (117) of handle assembly (11). The independent circuitry of the alternative battery pack may allow a battery pack to control when the battery pack provides power to its own circuitry and to control circuit (117); rather than allowing control circuit (117) to dictate when battery pack provides power to handle assembly (11), like battery pack (110) described above. Similarly, the alternative battery pack with independent circuitry may control when the battery pack provides power to motor (118), graphical user interface (116), or other suitable components of handle assembly (11). In other words, the alternative battery pack may independently shut down relative to handle assembly (11) or independently enter and control its own "sleep mode." The alternative battery pack may therefore prevent control circuit (117) from unnecessarily draining the power supply of the alternative battery pack. Additionally, the independent circuitry of the alternative battery pack may communicate with control circuit (117) to further exchange information. Examples of alternative battery packs will be described in greater detail below; while further examples will be apparent to those of ordinary skill in the art in view of the teachings herein.

A. Exemplary Alternative Handle Assembly and Battery Pack Assembly

Figure 7B:
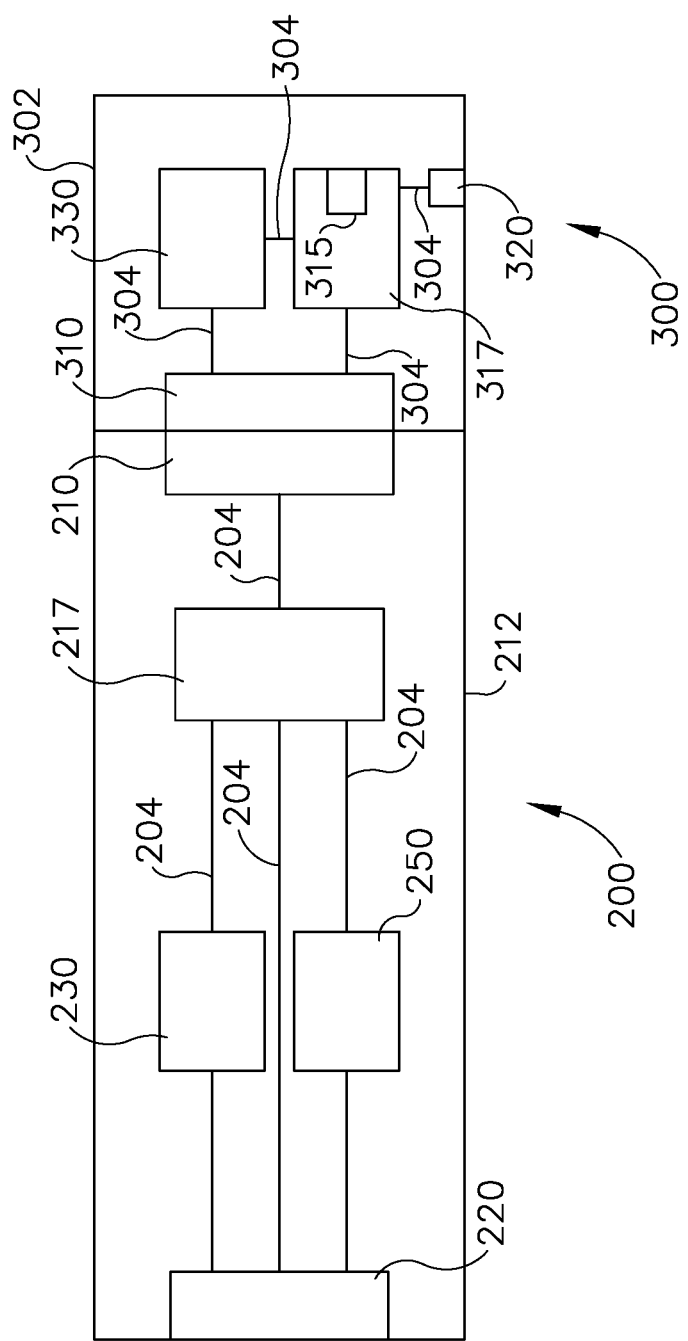
FIG. 7B depicts a schematic view of the handle assembly and battery pack of FIG. 7A, where the handle assembly and the battery pack are coupled to each other.
Figure 8:
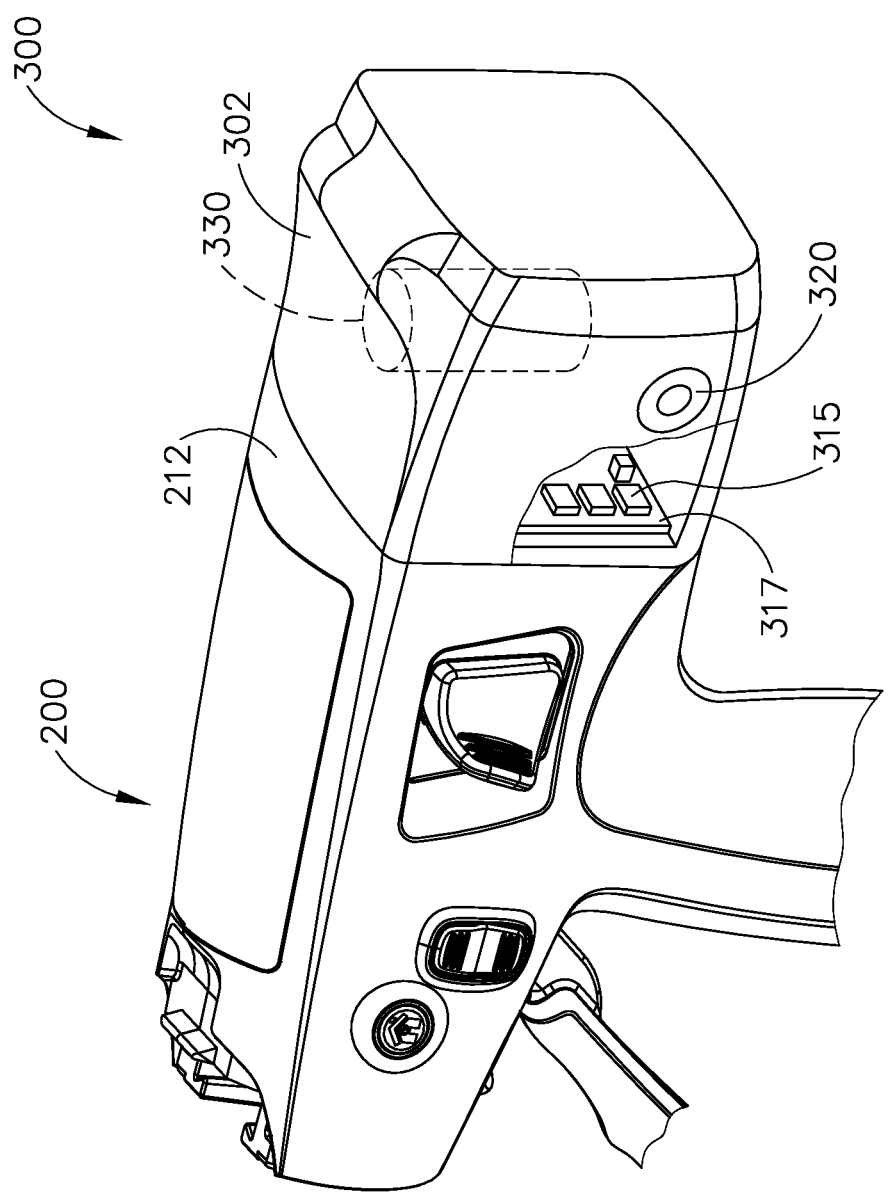
FIG. 8 depicts a partial perspective view of the handle assembly and battery pack of FIG. 7A, with a portion broken away to reveal internal components.

FIGS. 7A-8 show an exemplary handle assembly (200) and a complementary battery pack assembly (300) that may be readily incorporated into surgical instrument (10) in replacement of handle assembly (11) described above. Handle assembly (200) is substantially similar to handle assembly (11) assembly described above, with differences described below. Similarly, battery pack assembly (300) is substantially similar to battery pack (110) described above, with difference described below. As will be described in greater detail below, battery pack assembly (300) includes its own independent control circuit (317) controls when battery pack assembly (300) provides power to handle assembly (200), enters its own sleep mode, and/or communicates with handle assembly (200).

Handle assembly (200) includes a battery coupling assembly (210) while battery pack assembly (300) includes a handle coupling assembly (310). Battery coupling assembly (210) and handle coupling assembly (310) are configured to allow battery pack assembly (300) and handle assembly (200) to operatively engage each other such that battery pack assembly (300) may power suitable components of handle assembly (200). Therefore, when battery pack assembly (300) and handle assembly (200) are operatively disengaged via coupling assemblies (210, 310), battery pack assembly (300) may be prevented from powering suitable components of handle assembly (200). Coupling assemblies (210, 310) may include any suitable features used for operative engagement that would be apparent to one having ordinary skill in the art in view of the teachings herein. For example, coupling assemblies (210, 310) may include electrical connectors, similar to electrical connectors (106, 108) described above, that are used to establish electrical communication between handle assembly (11) and shaft assembly (16).

Handle assembly (200) and battery pack assembly (300) may also include any suitable features (e.g., latches, etc.) to mechanically attach to each other as would be apparent to one having ordinary skill in the art in view of the teachings herein. In the present example, as shown in FIGS. 7A-7B, battery pack assembly (300) may mechanically attach and detach from handle assembly (200) via features of respective coupling assemblies (310, 210). However, in some other versions, battery pack assembly (300) is not removable from handle assembly (200). In some such versions, battery pack assembly (300) (or a variation thereof) is fixed to, configured to permanently affix to, or fully contained within a housing (212) of handle assembly (200). Various suitable ways in which battery pack assembly (300) may couple to handle assembly (200) will be apparent to those of ordinary skill in the art in view of the teachings herein.

In addition to battery coupling assembly (210), handle assembly (200) further includes housing (212), a control circuit (217), a first drive system (230), a second drive system (250), and a shaft coupling assembly (220). Housing (212) is substantially similar to housing (12) described above. Control circuit (217) is substantially similar to control circuit (117) described above, with differences described below. Therefore, control circuit (217) may store and execute control algorithms, drive a graphical user interface, communicate with a connected shaft assembly (16), or any other suitable functions described above regarding control circuit (117). Control circuit (217) is in communication with battery coupling assembly (210) via electrical connection (204) such that control circuit (217) may receive power from battery pack assembly (300), and/or communicate with battery pack assembly (300), as will be described in greater detail below.

First drive system (230) is substantially similar to closure (first) drive system (30) described above. First drive system (230) may perform substantially the same functions of closure (first) drive system (30) as described above. Therefore, first drive system (230) may include a closure trigger substantially similar to closure trigger (32) described above, and any other components associated with closure (first) drive system (30). First drive system (230) may be in communication with control circuit (217) via electrical connection (204).

Second drive system (250) is substantially similar to the drive system of handle assembly (11) including motor (118). Therefore, second drive system (250) may include a motor that is controlled by control circuit (217). Additionally, second drive system (250) may include all other suitable components of handle assembly (11) used in conjunction with motor (118), as described above. Second drive system (250) may be in communication with control circuit (217) via electrical connection (204). In the current example, second drive system (250) may receive power from battery pack assembly (300) via control circuit (217), however, this is merely optional. Second drive system (250) may alternatively be directly connected to battery coupling assembly (210) to satisfy suitable power requirements. Any other suitable power connection between second drive system (250) and battery pack assembly (300) may be utilized as would be apparent to one having ordinary skill in the art in view of the teachings herein.

Shaft coupling assembly (220) is configured to selectively couple handle assembly (200) with shaft assembly (16) for operative engagement, similar to operative engagement between shaft assembly (16) and handle assembly (11) described above. Shaft coupling assembly (220) may include any suitable components similar to handle assembly (11) used to couple with shaft assembly (16) for operative engagement. Shaft coupling assembly (220) may interface with shaft assembly (16) such that first drive system (230) and second drive system (250) are operatively engaged with corresponding components of shaft assembly (16). Therefore, first drive system (230) and second drive system (250) may generate and apply various control motions to corresponding portions of shaft assembly (16) when operatively attached, similar to handle assembly (11) described above. Shaft coupling assembly (220) may be in communication with control circuit (217) via electrical connection (204) so that control circuit (217) may communicate with corresponding electrical components of shaft assembly (16), such as circuit board (not shown), via electrical connector (106).

Battery pack assembly (300) includes a casing (302), handle coupling assembly (310), control circuit (317), an accelerometer (315), a power button (320), and a power supply (330). As mentioned above, and as will be described in greater detail below, control circuit (317) is configured to control when battery pack assembly (300) provides power to handle assembly (200), enters its own sleep mode, and/or communicates with handle assembly (200). As will also be described in greater detail below, power button (320) and accelerometer (315) may be configured to command control circuit (317) to exit sleep mode to provide full power to handle assembly (200).

Power supply (330) is in communication with handle coupling assembly (310) and control circuit (317) via electrical wires (304). Control circuit (317) is also in communication with handle coupling assembly (310) via electrical wire (304). Control circuit (317) is operable to direct power supply (330) to power control circuit (317). Therefore, control circuit (317) may draw power from power supply (330) such that control circuit (317) may perform its intended functions as described herein. Control circuit (317) may also command selected portions of battery pack assembly (300) to operatively engage or operatively disengage selected portions of handle assembly (200). When handle assembly (200) and battery pack assembly (300) are operatively engaged via coupling assemblies (210, 310), power supply (330) may direct power to handle coupling assembly (310) such that power supply (330) may provide power to various components of handle assembly (200), such as control circuit (217). Additionally, when handle assembly (200) and battery pack assembly (300) are operatively engaged via coupling assemblies (210, 310), control circuit (317) may communicate with the corresponding control circuit (217) of handle assembly (200). Therefore, when handle assembly (200) and battery pack assembly (300) are operatively disengaged, power supply (330) may not direct power to components of handle assembly (200).

Control circuit (317) is an independent circuit that functions autonomously relative to control circuit (217) of handle assembly (200). Control circuit (317) may enter into its own sleep mode, similar to that described above for sleep mode of control circuit (117). Control circuit (317) of battery pack assembly (300) may have independent sleep algorithms, independent switching circuits, and independent control circuits that allow control circuit (317) of battery pack assembly (300) to completely or partially restrict power provided from power source (330) to itself as well as handle assembly (200) while in sleep mode. Therefore, control circuit (317) may control whether battery pack assembly (300) is operatively engaged or operatively disengaged with handle assembly (200). In other words, control circuit (317) is configured to control when power supply (330) may provide power to handle assembly (200) or control circuit (317). When control circuit (317) completely restricts power provided from power source (330) to handle assembly (200), handle assembly (200) may essentially shut down. Therefore, when control circuit (317) exits sleep mode to provide power to handle assembly (200), handle assembly (200) may reboot as if handle assembly (200) is receiving a new battery pack assembly (300). Control circuit (317) may also completely restrict power provided by power source (330) to control circuit (317) such that control circuit (317) uses no power as well.

In some instances while in sleep mode, control circuit (317) does not completely restrict power provided to itself by power source (330). In instances where control circuit (317) is not completely restricted from power, control circuit (317) may keep track of the duration through which battery pack assembly (300) is in sleep mode, temperature of battery pack assembly (300) while in sleep mode, and other suitable factors necessary such that control circuit (317) may calculate the estimated remaining battery life of power supply (330) as affected by the time and environment of battery pack assembly (300) while in sleep mode. Once control circuit (317) exits sleep mode and battery pack assembly (300) is returned to operative engagement with handle assembly (200), control circuit (317) may communicate the estimated remaining life to control circuit (217) of handle assembly (200). Handle assembly (200) may then display such information to an operator via a graphical user interface similar to graphical user interface (116) described above. This feature may be advantageous if control circuit (317) places handle assembly (200) and battery pack assembly (300) in sleep mode for prolonged periods of time. Of course, control circuit (317) may also keep track of time elapsed while battery pack assembly (300) is not in sleep mode, temperature of battery pack assembly (330) while not in sleep mode, and other suitable factors such that control circuit (317) may calculate estimated remaining battery life of power supply (330) as affected by the time, environment, and usage of battery pack assembly (300) while not is sleep mode.

As mentioned above, coupling assemblies (210, 310) may include any suitable features for operative engagement that would be apparent to one having skill in the art in view of the teachings herein, such as electrical connectors. In some instances, electrical connectors of coupling assemblies (210, 310) may physically disconnect from each other when battery pack assembly (300) and handle assembly (200) are operatively disengaged from each other. Therefore, electrical connectors of coupling assemblies (210, 310) may then physically reconnect to each other when battery pack assembly (300) and handle assembly (200) are operatively engaged with each other. This could be accomplished through any suitable means known to a person having ordinary skill in the art in view of the teachings herein. For example, battery pack assembly (300) may be spring loaded, or otherwise biased, such that electrical connectors of coupling assembly (310) are naturally disconnected from electrical connectors of coupling assembly (210), thereby rendering battery pack assembly (300) and handle assembly (200) operatively disengaged. When an operator desires to operatively engage battery pack assembly (300) and handle assembly (200), the operator may push battery pack assembly (300) toward handle assembly (200), overcoming the biasing force. A physical latch or electromagnetic force may then further overcome the biasing force to keep battery pack assembly (300) and handle assembly (200) operatively engaged without further assistance of an operator pushing battery pack assembly (300) toward handle assembly (200). When control circuit (317) is to go into sleep mode, the latching member or the electromagnet force may release, and the biasing force may return battery pack assembly (300) to the operatively disengaged position.

In the current example, power supply (330) is in direct communication with handle coupling assembly (310) such that power supply (330) may directly transfer power to handle coupling assembly (310). However, it should be understood this is merely optional. In some instances, power supply (330) may be in communication with handle coupling assembly (310) via control circuit (317). In other words, power supply (330) may transfer power to control circuit (317), which in turn may then transfer power to handle coupling assembly (310), which may in turn transfer power to suitable components of handle assembly (200) when operatively engaged.

As mentioned above, control circuit (317) may be configured to exchange information with control circuit (217) of handle assembly (200) when battery pack assembly (300) and handle assembly (200) are operatively engaged. In some instances, control circuit (217) of handle assembly (200) may communicate to control circuit (317) of battery pack assembly (300) that an operator has requested control circuit (317) go into sleep mode. An operator may request control circuit (317) go into sleep mode through any suitable user input that would be apparent to one having ordinary skill in the art in view of the teachings herein. Additionally, or alternatively, control circuit (217) may keep track of handle assembly (200) inactivity. If control circuit (217) determines that handle assembly (200) has been inactive for a predetermined amount of time, control circuit (217) may communicate a signal indicative of this inactivity to control circuit (317), causing control circuit (317) to initiate sleep mode.

While in some instances, handle assembly (200) may communicate to control circuit (317) to go into sleep mode, handle assembly (200) may also be restricted from communicating to control circuit (317) while in sleep mode, such that only battery pack assembly (300) may command control circuit (317) to exit sleep mode. As mentioned above, power button (320) and accelerometer (315) may be configured to command control circuit (317) to exit sleep mode and to provide full power to handle assembly (200). As seen in FIGS. 7A-7B, power button (320) is in communication with control circuit (317) via electrical wire (304). Power button (320) is accessible from an external portion of casing (302) such than an operator may easily access power button (320). If an operator desired to reactivate battery pack assembly (300) out of sleep mode, the operator may push power button (320), which may command control circuit (317) to exit sleep mode.

Accelerometer (315) is connected to control circuit (317), such that accelerometer (315) may detect and communicate movement of battery pack assembly (300) to control circuit (317). Accelerometer (315) may be configured to command control circuit (317) to exit sleep mode if accelerometer (315) detects movement above a predetermined threshold. When battery pack assembly (300) re-powers itself from exiting sleep mode, control circuit could check other control parameters before energizing handle assembly (200), such as a number of motions within a predefined time, or another accelerometer-detected change after power button (320) is pressed.

B. Exemplary Alternative Battery Pack Assembly

Figure 9:
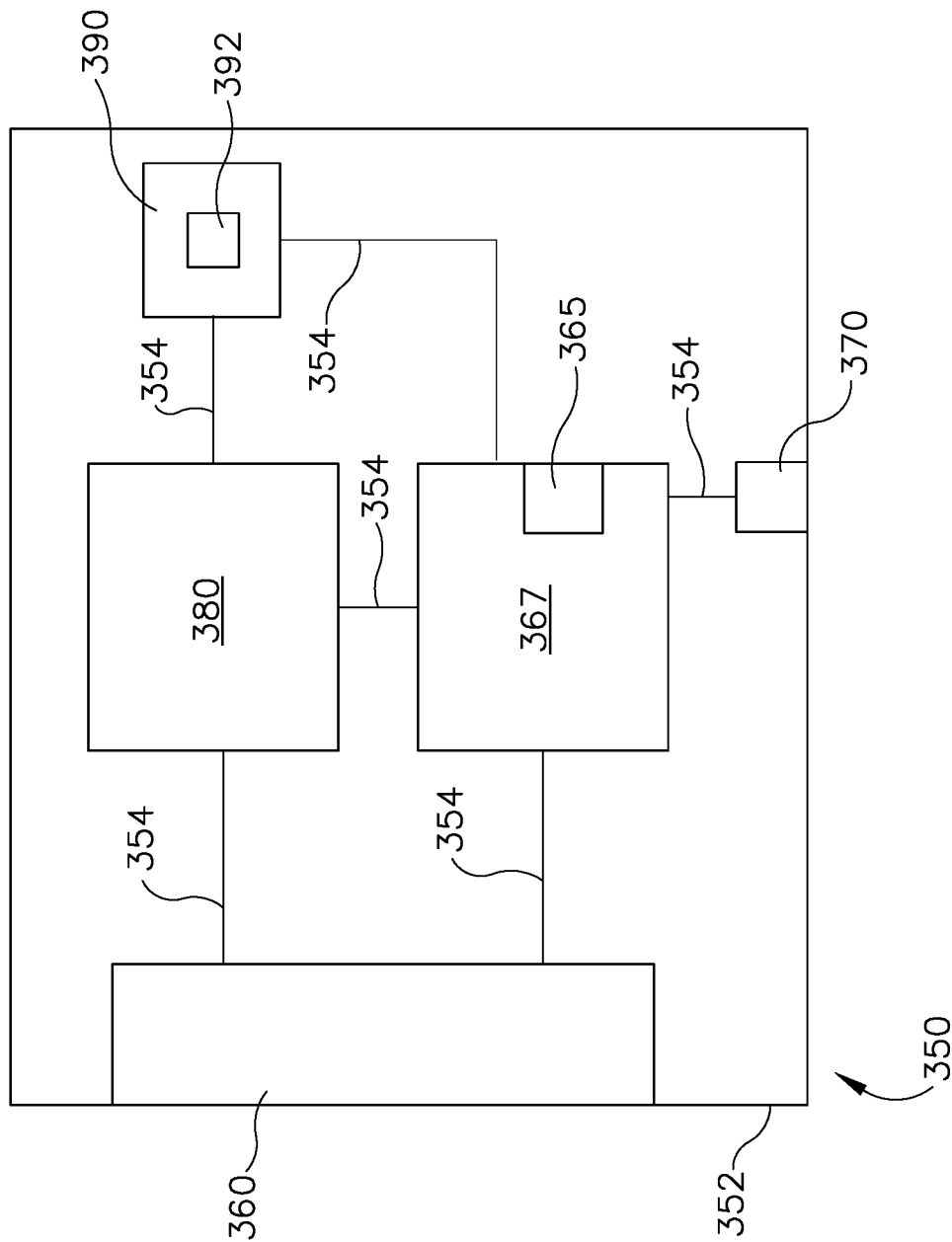
FIG. 9 depicts a schematic view of another exemplary alternative battery pack that may be readily incorporated into the handle assembly of FIG. 7A or the surgical instrument of FIG. 1.

FIG. 9 shows another alternative battery pack assembly (350) that may be readily incorporated into handle assembly (200) in replacement of battery pack assembly (300) described above. Battery pack assembly (350) is substantially similar to battery pack assembly (300) described above, with differences described below. Battery pack assembly (350) includes a casing (352), a handle coupling assembly (360), a power supply (380), a control circuit (367), an accelerometer (365), and a power button (370); which are substantially similar to casing (302), handle coupling assembly (310), power supply (330), control circuit (317), accelerometer (315), and power button (320) described above, respectively, with difference elaborated below. Control circuit (367) is in communication with power button (370), handle coupling assembly (360), and power supply (380) via electrical connections (354); while power supply (380) is in communication with handle coupling assembly (360) via electrical connection (354). Accelerometer (365) is in communication with control circuit (367).

Battery pack assembly (350) also includes a secondary control circuit (390) in communication with both power supply (380) and control circuit (367) via electrical connections (354). Secondary control circuit (390) includes its own independent power source (392), such that secondary control circuit (390) does not draw any power from power supply (380). Secondary control circuit (390) may include a low power micro controller. Independent power source (392) may include a coin battery cell that may keep secondary control circuit (390) in lower power mode such that secondary control circuit (390) does not draw any power from power supply (380) in a low power mode (i.e. when control circuit (317) is in sleep mode). Secondary control circuit (390) may be configured to calculate and/or archive the battery life remaining of power supply (380), similar to how control circuit (317) may calculate the battery life remaining of power supply (330) described above. Additionally, secondary control circuit (390) may receive information from control circuit (217) of handle assembly (200). For instance, control circuit (217) from handle assembly (200) may communicate to secondary control circuit (390) a remaining number of sterilization procedures to the non-volatile member of secondary control circuit (390) if handle assembly (200) is designed for multiple uses. Additionally, secondary control circuit (390) may be configured to exit low power mode from signals received by either control circuit (367, 217).

Additionally, secondary control circuit (390) may contain a very low electrical current drain range sleep mode monitoring circuit. When the electrical current range is measured as exceeding the range ability of the low drain circuit, secondary control circuit (390) could then poll the control circuit (367, 217) that contains the high range draw, and then control circuit (367, 217) could measure the battery life of power supply (380) from that point on. The communication linkage that allows the high range current measure from handle assembly (200) of battery pack assembly (300) may be the same linkage used to communicate usage from the handle assembly (200) and communicate uses left (after sterilization) back to the handle assembly (200) for display.

III. Exemplary Pre-Sterilization Fluid Distribution Assembly

Figure 10:
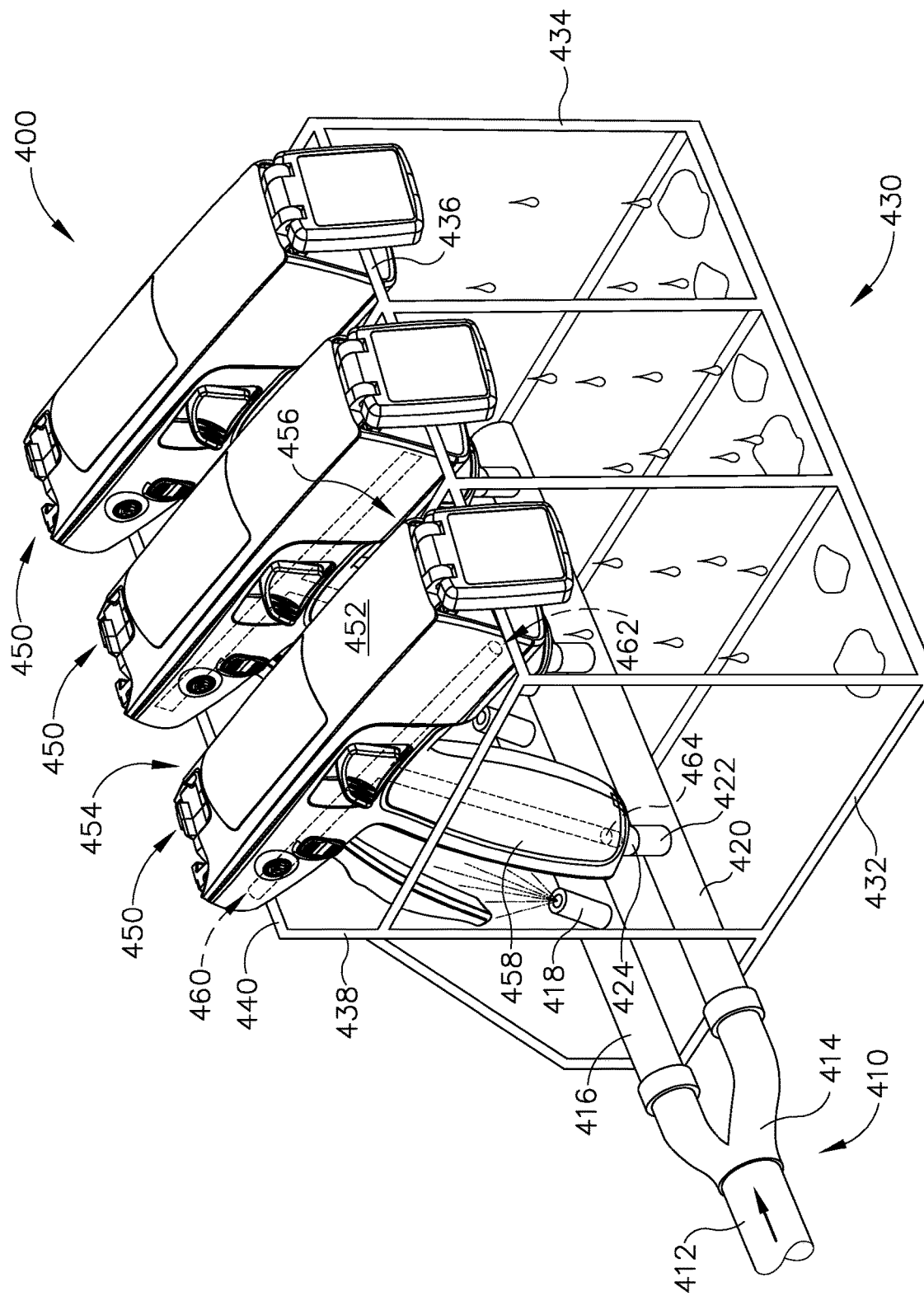
FIG. 10 depicts a perspective view of an exemplary pre-sterilization fluid distribution assembly.

In some instances, it may be desirable to perform a pre-sterilization cleaning procedure on handle assembly (11, 200) after a surgical procedure, either with or without battery pack (116, 300, 350) attached. A pre-sterilization cleaning procedure may flush out or remove excess debris on or within handle assembly (11, 200), thereby facilitating a subsequent sterilization procedure. FIG. 10 shows an exemplary pre-sterilization fluid distribution assembly (400) that may be used to perform a pre-sterilization cleaning procedure on handle assembly (11, 200) after a surgical procedure, and before a full sterilization process.

Pre-sterilization fluid distribution assembly (400) includes a manifold assembly (410), a support rack assembly (430), and a plurality of alternative handle assemblies (450). Handle assemblies (450) are substantially similar to handle assemblies (11, 200) described above, with difference elaborated below. Each handle assembly (450) includes a housing (452) extending from a distal portion (454) to a proximal portion (456), a pistol grip (458), internal fluid passageways (460) extending throughout housing (452), and quick connect fluid port (464). As will be described in greater detail below, quick connect fluid port (464) is configured to couple with a portion of manifold assembly (410) such that manifold assembly (410) is in fluid communication with internal fluid passageways (460). Handle assembly (450) also defines a drain port (462) located at proximal portion (456) of handle assembly (450) and also in fluid communication with internal fluid passageway (460). Drain port (462) allows fluid within internal fluid passageways (460) to escape. Internal fluid passageways (460) may be in fluid communication with any suitable portions of handle assembly (450) that need to be cleaned in a pre-sterilization cleaning procedure, such as portions that may potentially accumulate debris and/or fluids during operational use in a surgical procedure.

Handle assembly (450) may be designed such that handle assembly (450) does not accumulate debris and/or fluids during operational use in a surgical procedure. For instance, handle assembly (450) may be designed to avoid having pockets, crevices, etc. that will hold onto contaminants that are products of operational use. For instance, handle assembly (450) may be designed with large radii instead of tight corners. Additionally, handle assembly (450) may be designed to break into pieces to simplify cleaning. Internal fluid passageways (460) may take different paths for different components or difference levels of dirtiness. Therefore, internal fluid passageways (460) may be dimensioned to allow more fluid to go into locations requiting more cleaning during the pre-sterilization cleaning process. If handle assembly (450) includes a display, the display may easily pop out of handle assembly (450) prior to the pre-sterilization cleaning procedure. Additionally, the display could be behind a window in handle assembly (450) so that it does not come into direct contact with any contaminants. Handle assembly (450) may also include a means to sense when handle assembly (450) is ready for the sterilization process. In other words, handle assembly (450) may have a means to sense when handle assembly (450) has completed the pre-sterilization cleaning process, as described below. For instance, handle assembly may include a triaxial water sensor cupped to hold water, a super hydrophobic coating, a plurality of water sensors at the lowest points on each surface that can be the lowers points for water to settle into, or a window into handle assembly (450) to look for water and contaminants. Handle assembly (450) may indicate via the display when a sensor does not detect any more water.

Support rack assembly (430) is configured to support each handle assembly (450) such that drain port (462) may receive excess fluid from portions of internal fluid passageways (460). Support rack assembly (430) includes a base structure (432), a first plurality of vertical columns (434), a second plurality of vertical columns (438), a first top rail (436), and a second top rail (440). First plurality of vertical columns (434) extend from base structure (432) to first top rail (436) while second plurality of vertical columns (438) extend from an opposite end of base structure (432) to second top rail (440). Second top rail (440) is elevated higher than first top rail (436). Top rails (436, 440) are spaced apart a distance to support proximal portions (456) and distal portions (454) of handle assembly (450) respectively. In particular, top rails (436, 440) support handle assembly (450) such that handle assembly (450) is tilted at an angle conducive of gravity feeding excess fluid within portions of internal fluid passageways (460) toward drain ports (462).

Manifold assembly (410) and support rack assembly (430) are configured to work in tandem such that manifold assembly (410) may provide fluid communication to handle assembly (450) while support rack assembly (430) holds handle assemblies (450). Manifold assembly (410) includes a primary fluid supply tube (412) extending into a Y-fitting (414), which diverts fluid from fluid supply tube (412) into a first secondary fluid supply tube (416) and a second secondary fluid supply tube (420). First secondary fluid supply tube (416) has a plurality of external fluid distribution ports (418) while second secondary fluid supply tube (420) includes a plurality of internal fluid distribution ports (422) terminating into a quick connect fluid port (424).

External fluid distribution ports (418) are placed along first secondary fluid supply tube (416) such that external fluid distribution ports (418) align with respective handle assemblies (450). External fluid distribution ports (418) are configured to spray fluid on an exterior of handle assemblies (420). In particular, external fluid distribution ports (418) may spray any suitable washing media onto handle assembly (420) to wash off excess debris. Then external fluid distribution ports (418) may spray any suitable gas to dry off excess washing media accumulated on the exterior of handle assembly (420).

Internal fluid distribution ports (4212) are placed along second secondary fluid supply tube (420) such that quick connect fluid ports (424) may couple with quick connect fluid ports (464) of handle assembly (450). Quick connect fluid ports (424, 464) provide fluid communication between second secondary fluid supply tube (420) and internal fluid passageways (460) such that integral fluid distribution port (422) may supply internal fluid passages (460) with fluid for the pre-sterilization process. In particular, internal fluid distribution ports (422) may spray any suitable washing media into internal fluid passageways (460) of handle assembly (450) to wash off excess debris located within suitable locations of handle assembly (450). Then external fluid distribution ports (418) may spray any suitable gas to dry off excess washing media accumulated within the internal fluid passageways (460) of handle assembly (420). Quick connect fluid ports (424, 464) may include one way valves that allow fluid to enter within internal fluid passageways (460), but prevents fluid from exiting internal fluid passageways (460) back into secondary second fluid supply tube (420).

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples, Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) handle assembly, wherein the handle assembly comprises: (i) a housing, and (ii) a first control circuit located within the housing; and (b) a battery pack assembly, wherein the battery pack assembly comprises: (i) a power supply configured to selectively transition from a first state to a second state, wherein the power supply is configured to energize the first control circuit of the handle assembly in the first state, wherein the power supply is configured to not energize the first control circuit of the handle assembly in the second state, and (ii) a second control circuit in communication with the power supply, wherein the second control circuit is configured to transition the power supply between the first state and the second state.

Example 2

The apparatus of Example 1, wherein the handle assembly further comprises a first coupling assembly in communication with the first control circuit, wherein the battery pack assembly further comprises a second coupling assembly configured to communicate with the first coupling assembly of the handle assembly such that the power supply may selectively energize the first control circuit.

Example 3

The apparatus of Example 2, wherein the second control circuit is in communication with the second coupling assembly.

Example 4

The apparatus of any one or more of Examples 2 through 3, wherein the first coupling assembly comprises a first set of electrical contacts, wherein the second coupling assembly comprises a second set of electrical contacts.

Example 5

The apparatus of any one or more of Examples 2 through 4, wherein the first coupling assembly is configured to selectively attach with the second coupling assembly.

Example 6

The apparatus of any one or more of Examples 1 through 5, wherein the battery pack assembly further comprises a power button in communication with the second control circuit, wherein the power button is configured to instruct the second control circuit to transition the power supply from the second state to the first state in response to activation of the power button.

Example 7

The apparatus any one or more of Examples 1 through 6, wherein the battery pack assembly further comprises an accelerometer in communication with the second control circuit, wherein the accelerometer is configured to detect movement of the battery pack assembly, wherein the accelerometer is configured to instruct the second control circuit to transition the power supply from the second state to the first state in response to the accelerometer detecting movement of the battery pack assembly.

Example 8

The apparatus of any one or more of Examples 1 through 7, second control circuit is configured to draw power from the power source when the power source is in the second state.

Example 9

The apparatus of Example 8, wherein the second control circuit is configured to calculate an estimated battery life of the power source while the power source is in the second state.

Example 10

The apparatus of Example 9, wherein the second control circuit is configured to track a time value associated with the power source in the second state.

Example 11

The apparatus of any one or more of Examples 9 through 10, wherein the second control circuit is configured to track a temperature value associated with the power source in the second state.

Example 12

The apparatus of any one or more of Examples 1 through 11, wherein the first control circuit and the second control circuit are in communication while the power source is in the first state.

Example 13

The apparatus of Example 12, wherein the first control circuit is configured to instruct the second control circuit to transition the power source from the first state to the second state.

Example 14

The apparatus of Example 13, wherein the first control circuit is prohibited from instructing the second control circuit to transition the power source from the second state to the first state.

Example 15

The apparatus of any one or more of Examples 1 through 14, further comprising a modular shaft, wherein the handle assembly further comprises a shaft coupling assembly configured to selectively couple with the modular shaft.

Example 16

The apparatus of Example 15, wherein the first control circuit is configured to communicate with the modular shaft when the handle assembly is coupled with the modular shaft.

Example 17

An apparatus, comprising: (a) handle assembly, wherein the handle assembly comprises: (i) a housing, and (ii) a first control circuit located within the housing; (b) a power supply configured to selectively transition from a first state to a second state, wherein the power supply is configured to energize the first control circuit of the handle assembly in the first state, wherein the power supply is not in communication with the first control circuit of the handle assembly in the second state; and (c) a second control circuit in communication with the power supply, wherein the second control circuit is configured to transition the power supply from the second state to the first state.

Example 18

The apparatus of Example 17, wherein second control circuit is configured to transition the power supply from the first state to the second state.

Example 19

The apparatus of Example 18, wherein the first circuit is configured to communicate with the second circuit when the power supply is in the first state.

Example 20

An apparatus, comprising: (a) handle assembly, wherein the handle assembly comprises: (i) a housing, (ii) a shaft coupling assembly, and (ii) a first control circuit located within the housing; (b) a modular shaft configured to selectively couple with the shaft coupling assembly of the handle assembly, wherein the modular shaft includes a distal end having an end effector that is configured to operate on tissue; and (c) a battery assembly comprising: (i) a power supply configured to selectively transition from a first state to a second state, wherein the power supply is configured to energize the first control circuit of the handle assembly in the first state, wherein the power supply is not in communication with the first control circuit of the handle assembly in the second state, and (ii) a second control circuit in communication with the power supply, wherein the second control circuit is configured to transition the power supply from the second state to the first state.

V. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

In addition to the foregoing, the teachings herein may be readily combined with the teachings of U.S. patent application Ser. No. 15/634,385, entitled "Apparatus and Method to Determine End of Life of Battery Powered Surgical Instrument," filed on even date herewith, the disclosure of which is incorporated by reference herein. Various suitable ways in which the teachings herein may be combined with the teachings of U.S. patent application Ser. No. 15/634,685 will be apparent to those of ordinary skill in the art in view of the teachings herein.

In addition to the foregoing, the teachings herein may be readily combined with the teachings of U.S. patent application Ser. No. 15/634,418, entitled "Surgical Instrument with integrated and Independently Powered Displays," filed on even date herewith, the disclosure of which is incorporated by reference herein. Various suitable ways in which the teachings herein may be combined with the teachings of U.S. patent application Ser. No. 15/634,418 will be apparent to those of ordinary skill in the art in view of the teachings herein.

In addition to the foregoing, the teachings herein may be readily combined with the teachings of U.S. patent application Ser. No. 15/634,452, entitled "Battery Powered Surgical Instrument with Dual Power Utilization Circuits for Dual Modes," filed on even date herewith, the disclosure of which is incorporated by reference herein. Various suitable ways in which the teachings herein may be combined with the teachings of U.S. patent application Ser. No. 15/364,452 will be apparent to those of ordinary skill in the art in view of the teachings herein.

In addition to the foregoing, the teachings herein may be readily combined with the teachings of U.S. patent application Ser. No. 15/634,475, entitled "Powered Surgical instrument with Latching Feature Preventing Removal of Battery Pack," filed on even date herewith, the disclosure of which is incorporated by reference herein. Various suitable ways in which the teachings herein may be combined with the teachings of U.S. patent application Ser. No. 15/364,475 will be apparent to those of ordinary skill in the art in view of the teachings herein.

In addition to the foregoing, the teachings herein may be readily combined with the teachings of U.S. patent application Ser. No. 15/634,497, entitled "Modular Powered Electrical Connection for Surgical Instrument with Features to Prevent Electrical Discharge" filed on even date herewith, the disclosure of which is incorporated by reference herein. Various suitable ways in which the teachings herein may be combined with the teachings of U.S. patent application Ser. No. 15/634,497 will be apparent to those of ordinary skill in the art in view of the teachings herein.

In addition to the foregoing, the teachings herein may be readily combined with the teachings of U.S. patent application Ser. No. 15/634,524, entitled "Powered Surgical Instrument with Independent Selectively Applied Rotary and Linear Drivetrains," filed on even date herewith, the disclosure of which is incorporated by reference herein. Various suitable ways in which the teachings herein may be combined with the teachings of U.S. patent application Ser. No. 15/634,524 will be apparent to those of ordinary skill in the art in view of the teachings herein.

In addition to the foregoing, the teachings herein may be readily combined with the teachings of U.S. patent application Ser. No. 15/634,556, entitled "Powered Circular Stapler with Reciprocating Drive Member to Provide Independent Stapling and Cutting of Tissue," filed on even date herewith, the disclosure of which is incorporated by reference herein. Various suitable ways in which the teachings herein may be combined with the teachings of U.S. patent application Ser. No. 15/634,556 will be apparent to those of ordinary skill in the art in view of the teachings herein.

In addition to the foregoing, the teachings herein may be readily combined with the teachings of U.S. patent application Ser. No. 15/634,620, entitled "Surgical Stapler with Independently Actuated Drivers to Provide Varying Staple Heights," filed on even date herewith, the disclosure of which is incorporated by reference herein. Various suitable ways in which the teachings herein may be combined with the teachings of U.S. patent application Ser. No. 15/634,620 will be apparent to those of ordinary skill in the art in view of the teachings herein.

In addition to the foregoing, the teachings herein may be readily combined with the teachings of U.S. patent application Ser. No. 15/634,589, entitled "Surgical Instrument Handle Assembly with Feature to Clean Electrical Contacts at Modular Shaft Interface," filed on even date herewith, the disclosure of which is incorporated by reference herein. Various suitable ways in which the teachings herein may be combined with the teachings of U.S. patent application Ser. No. 15/634,589 will be apparent to those of ordinary skill in the art in view of the teachings herein.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
   (a) a handle assembly including:
      (i) a housing,
      (ii) a first control circuit located within the housing, and
      (iii) an actuator movably coupled to the housing and configured to manipulate an end effector of the apparatus; and
   (b) a battery pack assembly including:
      (i) a power supply configured to store an electrical charge,
      (ii) a second control circuit in communication with the power supply and the first control circuit, wherein the second control circuit is configured to transition between a first state and a second state, and
      (iii) a power activation input positioned on an exterior of the battery pack assembly, wherein the power activation input is operable to transition the second control circuit from the second state to the first state,
   wherein in the first state the second control circuit is configured to transfer the electrical charge from the power supply to the first control circuit,
   wherein in the second state the second control circuit is configured to at least partially withhold the electrical charge from the first control circuit.

2. The apparatus of claim 1, wherein the handle assembly further comprises a first coupling assembly in communication with the first control circuit, wherein the battery pack assembly further comprises a second coupling assembly configured to communicate with the first coupling assembly of the handle assembly such that the power supply may selectively transfer the electrical charge to the first control circuit.

3. The apparatus of claim 2, wherein the second control circuit is in communication with the second coupling assembly.

4. The apparatus of claim 2, wherein the first coupling assembly comprises a first set of electrical contacts, wherein the second coupling assembly comprises a second set of electrical contacts.

5. The apparatus of claim 2, wherein the first coupling assembly is configured to selectively attach with the second coupling assembly.

6. The apparatus of claim 1, wherein the power activation input includes a power button.

7. The apparatus of claim 1, wherein the battery pack assembly further comprises an accelerometer in communication with the second control circuit, wherein the accelerometer is configured to detect movement of the battery pack assembly, wherein the accelerometer is configured to instruct the second control circuit to transition from the second state to the first state in response to the accelerometer detecting movement of the battery pack assembly.

8. The apparatus of claim 1, wherein the second control circuit is configured to draw electrical charge from the power supply in the second state.

9. The apparatus of claim 8, wherein the second control circuit is configured to calculate an estimated battery life of the power supply while in at least one of the first state and the second state.

10. The apparatus of claim 9, wherein the second control circuit is configured to track a time value associated with the power supply while in the second state.

11. The apparatus of claim 9, wherein the second control circuit is configured to track a temperature value associated with the power supply while in the second state.

12. The apparatus of claim 1, wherein the first control circuit and the second control circuit are in communication while the second control circuit is in the first state.

13. The apparatus of claim 12, wherein the first control circuit is configured to instruct the second control circuit to transition from the first state to the second state.

14. The apparatus of claim 13, wherein the first control circuit is prohibited from instructing the second control circuit to transition from the second state to the first state.

15. An apparatus, comprising:
(a) a handle assembly including:
  (i) a housing, and
  (ii) a first control circuit located within the housing;
(b) a power supply configured to provide power; and
(c) a second control circuit in communication with the power supply and the first control circuit, wherein the second control circuit is configured to transition between a first state and a second state,
wherein in the first state the second control circuit is configured to electrically couple the power supply to the first control circuit,
wherein in the second state the second control circuit is configured to electrically uncouple the power supply from the first control circuit.

16. The apparatus of claim 15, wherein the second control circuit in the second state is configured to permit transfer of power from the power supply to the second control circuit and simultaneously fully restrict transfer of power from the power supply to the first control circuit.

17. The apparatus of claim 16, wherein the first control circuit is configured to communicate with the second control circuit while the second control circuit is in the first state.

18. An apparatus, comprising:
(a) a handle assembly including:
  (i) a housing,
  (ii) a shaft coupling assembly,
  (iii) a first control circuit located within the housing, and
  (iv) an actuator movably coupled to the housing and configured to manipulate an end effector of the apparatus;
(b) a modular shaft configured to selectively couple with the shaft coupling assembly of the handle assembly, wherein the modular shaft includes a distal end having an end effector that is configured to operate on tissue; and
(c) a battery assembly including:
  (i) a power supply configured to provide power,
  (ii) a power actuator accessible from an exterior of the battery assembly, and
  (iii) a second control circuit in communication with the power supply and the first control circuit, wherein the second control circuit is configured to transition between a first state and a second state,
  wherein in the first state the second control circuit is configured to transfer the power to the first control circuit,
  wherein in the second state the second control circuit is configured to limit transfer of the power from the power supply to the first control circuit and the second control circuit,
  wherein the second control circuit is configured to transition from the second state to the first state in response to an actuation of the power actuator.

19. The apparatus of claim 1, further comprising a third control circuit in communication with the power supply and the second control circuit, wherein the third control circuit includes a low-power microcontroller.

20. The apparatus of claim 1, further comprising a third control circuit in communication with the power supply and the second control circuit, wherein the third control circuit is configured to calculate an estimated battery life of the power supply while in the second state.

* * * * *